(12) United States Patent
Bunquin et al.

(10) Patent No.: US 10,391,477 B2
(45) Date of Patent: Aug. 27, 2019

US010391477B2

(54) MULTIMETALLIC CATALYSTS

(71) Applicant: UCHICAGO ARGONNE, LLC, Chicago, IL (US)

(72) Inventors: Jeffrey C. Bunquin, Westmont, IL (US); Magali S. Ferrandon, Downers Grove, IL (US); Massimiliano Delferro, Chicago, IL (US); Peter C. Stair, Northbrook, IL (US)

(73) Assignee: UChicago Argonne, LLC, Chicago, IL (US)

( * ) Notice: Subject to any disclaimer, the term of this patent is extended or adjusted under 35 U.S.C. 154(b) by 0 days.

(21) Appl. No.: 15/691,677

(22) Filed: Aug. 30, 2017

(65) Prior Publication Data

US 2018/0093253 A1 Apr. 5, 2018

Related U.S. Application Data

(60) Provisional application No. 62/402,218, filed on Sep. 30, 2016.

(51) Int. Cl.
*B01J 23/60* (2006.01)
*C07C 5/333* (2006.01)

(52) U.S. Cl.
CPC ............ *B01J 23/60* (2013.01); *C07C 5/3332* (2013.01); *C07C 5/3337* (2013.01); *C07C 2521/02* (2013.01); *C07C 2521/04* (2013.01); *C07C 2521/08* (2013.01); *C07C 2523/42* (2013.01); *C07C 2523/60* (2013.01)

(58) Field of Classification Search
CPC .... C07C 11/167; C07C 5/3335; C07C 5/3337
See application file for complete search history.

(56) References Cited

U.S. PATENT DOCUMENTS

| | | | |
|---|---|---|---|
| 3,539,651 A | 11/1970 | Hepp et al. | |
| 4,005,985 A | 2/1977 | Hutson, Jr. | |
| 4,041,099 A | 8/1977 | Hutson, Jr. | |
| 4,176,140 A | 11/1979 | Bertus et al. | |
| 6,191,064 B1 | 2/2001 | Wu et al. | |
| 6,414,209 B1 | 7/2002 | Herskowitz et al. | |
| 6,635,598 B2 | 10/2003 | Dongara et al. | |
| 6,756,340 B2 | 6/2004 | Voskoboynikov et al. | |
| 7,034,195 B2 * | 4/2006 | Schindler ............... | C07C 5/3335 585/616 |
| 7,972,569 B2 | 7/2011 | Elam et al. | |
| 8,318,248 B2 | 11/2012 | Elam et al. | |
| 2013/0072738 A1 | 3/2013 | Jung et al. | |
| 2014/0309470 A1 | 10/2014 | Park et al. | |

FOREIGN PATENT DOCUMENTS

| | | |
|---|---|---|
| CN | 102417432 A | 4/2012 |
| DE | 20 26 104 A1 | 12/1970 |
| DE | 24 01 955 A1 | 7/1975 |
| EP | 0 986 22 A2 | 1/1984 |
| EP | 2 832 716 A1 | 2/2015 |
| GB | 0 904 699 A | 8/1962 |
| IT | 1409944 B1 | 9/2014 |
| KR | 1020140013387 A | 2/2014 |
| KR | 1020140085776 A | 7/2014 |
| KR | 1477413 B1 | 12/2014 |
| KR | 1020140143591 A | 12/2014 |
| KR | 2015037503 A | 4/2015 |
| KR | 101485697 B1 | 1/2016 |
| WO | WO-2014/128717 A2 | 8/2014 |

OTHER PUBLICATIONS

Ajayi, et al., "n-Butane dehydrogenation over mono and bimetallic MCM-41 catalysts under oxygen free atmosphere," Catalysis Today 204, pp. 189-196 (2013).
Ballarini, et al., "Use of Al2O3—SnO2 as a support of Pt for selective dehydrogenation of light paraffins," Catalysis Today 133-135, pp. 28-34 (2008).
Bocanegra, et al., "Behavior of PtPb/MgAl2O4 catalysts with different Pb contents and trimetallic PtPbIn catalysts in n-butane dehydrogenation," Applied Catalysis A: General 468, pp. 135-142 (2013).
Bocanegra, et al., "Characterization and catalytic behavior in the n-butane dehydrogenation of trimetallic InPtSn/MgAl2O4 catalysts," Applied Catalysis A: General, pp. 49-56 (2007).
Bocanegra, et al., "Effect of the Synthesis Method of MgAl2O4 and of Sn and Pb Addition to Platinum Catalysts on the Behavior in n-Butane Dehydrogenation," Industrial & Engineering Chemistry Research 49(9), pp. 4044-4054 (2010).
Bocanegra, et al., "n-Butane Dehydrogenation on PtSn Supported on MAl2O4 (M: Mg or Zn) Catalysts," Catalysis Letters 96(3-4), pp. 129-140 (2004).
Callejas, et al., "Catalytic dehydrogenation of n-butane in a fluidized bed reactor with separate coking and regeneration zones," Studies in Surface Science and Catalysis 130, pp. 2717-2722 (2000).
Chen, et al,. "Butane Dehydrogenation Reaction on Sulfur Poisoned Group 10 Metal/SiO2 Catalysts," Journal of the Chinese Chemical Society 43(5), pp. 379-386 (1996).
Huang, et al., "Optimization of process conditions for butane dehydrogenation catalyst L-78," Shihua Jishu Yu Yingyong (Petrochemical Technology & Application) 32(2), pp. 131-134 (2014).
Inaba, et al., "Dehydrogenation and Isomerization of n-Butane or Isobutane Over Cr Catalysts Supported on Zeolites," Catalysis Letters 84(3-4), pp. 273-279 (2002).
Kikuchi, et al., "Dehydrogenation of n-Butane to Butadiene over Pt—Sn/MgO—Al2O3," Journal of the Japan Petroleum Institute 55(1), pp. 33-39 (2012).
Kikuchi, et al., "Effect of Sn Addition on n-Butane Dehydrogenation over Alumina-supported Pt Catalysts Prepared by Co-impregnation and Sol-gel Methods," Journal of the Japan Petroleum Institute 55(3), pp. 206-213 (2012).
Larese, et al., "Alumina- and Zirconia-Alumina-Loaded Tin-Platinum. Surface Features and Performance for Butane Dehydrogenation," Langmuir 16(25), pp. 10294-10300 (2000).
Lee, et al., "Platinum-Tin Nano-Catalysts Supported on Alumina for Direct Dehydrogenation of n-Butane," Journal of Nanoscience and Nanotechnology 15(10), pp. 8305-8310 (2015).

(Continued)

*Primary Examiner* — Sharon Pregler
(74) *Attorney, Agent, or Firm* — Foley & Lardner LLP

(57) ABSTRACT

A multimetallic catalyst having a substrate, promoter and catalytic metal.

19 Claims, 39 Drawing Sheets

(56) References Cited

OTHER PUBLICATIONS

Loc, et al., "Kinetics of Propane and n-Butane Dehydrogenation over Platinumframe0Alumina Catalysts in the Presence of Hydrogen and Water Vapor," Kinetika i Kataliz (Kinetics and Catalysis) 37(60), pp. 790-796 (1996).

Megumu, et al., "Dehydrogenation and Isomerization of Butane over Cr Catalysts Supported on H-SSZ-35 Type Zeolites," Bulletin of the Chemical Society of Japan 77(2), pp. 381-386 (2004).

Nagaraja, et al., "Selective and stable bimetallic PtSn/θ-Al2O3 catalyst for dehydrogenation of n-butane to n-butenes," Applied Catalysis A: General 467, pp. 211-223 (2013).

Seo, et al., "Direct dehydrogenation of n-butane over Pt/Sn/M/ý—Al2O3 catalysts: Effect of third metal (M) addition," Catalysis Communications 47, pp. 22-27 (2014).

Seo, et al., "Direct Dehydrogenation of n-Butane Over Pt/Sn/Zn/ý-Al2O3 Nano-Catalyst: Effect of Zn Content," Journal of Nanoscience and Nanotechnology 15(10), pp. 8318-8323 (2015).

Shashikala, et al., "n-Butane Dehydrogenation on PtSn/Carbon Modified MgO Catalysts," Catalysis Letters 143(7), pp. 651-656 (2013).

Volpe, et al., "Butane dehydrogenation on vanadium supported catalysts under oxygen free atmosphere," Applied Catalysis A: General 272(1-2), pp. 69-78 (2004).

Wakui, et al., "Dehydrogenative Cracking of n-Butane over Modified HZSM-5 Catalysts," Catalysis Letters 81(1-2), pp. 83-88 (2002).

Wu & Stair, "UV Raman spectroscopic studies of V/θ-Al2O3 catalysts in butane dehydrogenation," Journal of Catalysis 237(2), pp. 220-229 (2006).

Wu, et al., "n-Butane dehydrogenation over Pt/Mg(In)(Al)O," Applied Catalysis A: General 470, pp. 208-214 (2014).

* cited by examiner

US 10,391,477 B2

MULTIMETALLIC CATALYSTS

CROSS-REFERENCE TO RELATED APPLICATIONS

This application claims benefit of U.S. Provisional Patent Application No. 62/402,218 filed Sep. 30, 2016, the content of which is incorporated herein by reference in its entirety.

STATEMENT OF GOVERNMENT INTEREST

The United States Government has rights in the invention described herein pursuant to Contract No. DE-AC02-06CH11357 between the United States Department of Energy and UChicago Argonne, LLC, as operator of Argonne National Laboratory.

FIELD OF THE INVENTION

The present invention generally relates to catalysts, specifically to multimetallic catalysts.

BACKGROUND OF THE INVENTION

Catalysts provide a vital mechanism for facilitating modern industrial-scale chemical production. This is particularly true in petrochemical processing and organics production. The changing demand for specific hydrocarbon products as well as the changing oil feedstock due to shale oil production in competition with traditional crude oil. Catalytic n-butane dehydrogenation is very important for the production of butenes (for example, 1-butene and cis/trans 2-butene) and 1,3-butadiene. In particular, the latter product is important as a precursor for fine-chemical synthesis and both are important for polymer production.

Ideally, catalysts facilitate chemical transformations with a selectivity for desired reactions (and end products) and a practical stability or lifetime before the catalyst is fouled or deactivated. For n-butane dehydrogenation, platinum and platinum group materials have long been used as catalysts. However, energy-intensive nature of the dehydrogenation reaction (typically requiring harsh conditions) has been shown detrimental to the long-term stability and overall efficiency of these platinum catalysts. While high-surface-area substrates, such as silica and alumina, have been utilized as supports for platinum catalysts, such catalysts deactivate as a result of active-site sintering. In particular, silica supports have been considered as poor performers due to the more facile catalyst sintering. For example, U.S. Pat. No. 4,041,099 highlights problems with silica as a support and stresses the use of a silica-free process. Alumina also exhibits undesirable characteristics such as a Lewis acid behavior resulting in cracking into lower value hydrocarbon fragments (C1, C2, and C3).

There is a need for a platinum group catalyst that utilizes high-surface area substrates while maintaining catalyst activity, selectivity and stability.

SUMMARY OF THE INVENTION

In one embodiment, a catalyst for n-butane dehydrogenation comprising: a substrate surface consisting essentially of an oxide; a promoter consisting essentially of $MO_x$ where M is a transition metal or main group elemental oxide, the promoter deposited on the substrate; a catalytic metal consisting essentially of a platinum group metalpromoter.

A method of forming 1,3-butadiene comprising: exposing n-butane to a catalyst comprising $M'/M/E_xO_y$ where the catalyst M' is a Pt group metal, M is a transition metal or a main group element material and E is Si, Al, Ti, or Zr and x and y represent stoichiometric amounts; forming 1,3 butadiene.

A method of forming 1,3-butadiene comprising: exposing 1-butene to a catalyst comprising $M'/M/E_xO_y$ where the catalyst M' is a Pt group metal, M is a transition metal or a main group element material and E is Si, Al, Ti, or Zr and x and y represent stoichiometric amounts; forming 1,3-butadiene.

Additional features, advantages, and embodiments of the present disclosure may be set forth from consideration of the following detailed description, drawings, and claims. Moreover, it is to be understood that both the foregoing summary of the present disclosure and the following detailed description are exemplary and intended to provide further explanation without further limiting the scope of the present disclosure claimed.

BRIEF DESCRIPTION OF THE DRAWINGS

The foregoing and other objects, aspects, features, and advantages of the disclosure will become more apparent and better understood by referring to the following description taken in conjunction with the accompanying drawings, in which:

FIG. 2A is a graph of selectivity to 1,3-butadiene at 500° C. FIG. 2B is a graph of selectivity to 1-butene at 500° C. FIG. 2C is a graph of selectivity to cis-2-butene at 500° C. FIG. 2D is a graph of selectivity to trans-2-butene at 500° C. Experimental conditions: Catalysts: 10 mg diluted with 100 mg $SiO_2$; Pre-activation: The catalysts were pre-activated at 550° C. for 2 h using 10% $H_2$ in $N_2$; Catalysis Feed: 1% N-butane in Ar (100 mL/min)+He (16 mL/min) for 16 reactors; Reaction Temperature: 500° C.

FIG. 4A is a graph of selectivity to 1,3-butadiene at 500° C. FIG. 4B is a graph of selectivity to cis-2-butadiene at 500° C. FIG. 4C is a graph of selectivity to trans-2-butadiene at 500° C. Experimental conditions: Catalysts: 10 mg diluted with 100 mg $SiO_2$; Pre-activation: The catalysts were preactivated at 550° C. for 2 h using 10% $H_2$ in $N_2$; Catalysis Feed: 1% N-butane in Ar (100 mL/min)+He (16 mL/min) for 16 reactors; Reaction Temperature: 500° C.

FIG. 5A shows n-Butane dehydrogenation activity of a catalyst synthesized using solution-phase synthesis methods. FIG. 5B shows n-Butane dehydrogenation activity of a catalyst synthesized via ALD. FIG. 5C shows n-Butane dehydrogenation activity of a PtZn catalyst with B as dopant synthesized by ALD. FIG. 5D shows n-Butane dehydrogenation activity of a Pt catalyst with B as dopant prepared via solution-phase synthesis methods.

FIG. 6A shows selectivity to 1,3-butadiene from n-butane dehydrogenation at 450° C. using the catalysts described in FIGS. 5A-5D. FIG. 6B shows selectivity to 1,3-butadiene from n-butane dehydrogenation at 500° C. FIG. 6C shows selectivity to 1,3-butadiene from n-butane dehydrogenation at 550° C. using the catalysts described in FIGS. 5A-5D. FIG. 6D shows selectivity to 1,3-butadiene from n-butane dehydrogenation at 600° C.

FIG. 7A shows selectivity to 1-butene from n-butane dehydrogenation at 450° C. using the catalysts described in FIG. 5A-5D. FIG. 7B shows selectivity to 1-butene from n-butane dehydrogenation at 500° C. FIG. 7C shows selectivity to 1-butene from n-butane dehydrogenation at 550° C. FIG. 7D shows selectivity to 1-butene from n-butane dehydrogenation at 600° C.

FIG. 8A shows selectivity to cis-2-butene from n-butane dehydrogenation at 450° C. using the catalysts described in FIG. 5A-5D. FIG. 8B shows selectivity to cis-2-butene from n-butane dehydrogenation at 500° C. FIG. 8C shows selectivity to cis-2-butene from n-butane dehydrogenation at 550° C. FIG. 8D shows selectivity to cis-2-butene from n-butane dehydrogenation at 600° C.

FIG. 9A shows selectivity to trans-2-butene from n-butane dehydrogenation at 450° C. using the catalysts described in FIG. 5A-5D. FIG. 9B shows selectivity to trans-2-butene from n-butane dehydrogenation at 500° C. FIG. 9C shows selectivity to trans-2-butene from n-butane dehydrogenation at 550° C. FIG. 9D shows selectivity to trans-2-butene from n-butane dehydrogenation at 600° C.

FIG. 10A shows spent catalysts showing different degrees of coke deposition n-butane dehydrogenation at 450° C. FIG. 10B shows spent catalysts showing different degrees of coke deposition n-butane dehydrogenation at 500° C. FIG. 10C shows spent catalysts showing different degrees of coke deposition n-butane dehydrogenation at 550° C. FIG. 10D shows spent catalysts showing different degrees of coke deposition after n-butane dehydrogenation at 600° C.

FIG. 11A shows spent catalysts showing different degrees of coke deposition after 1-butene dehydrogenation at 500° C.

FIG. 11B shows spent catalysts showing different degrees of coke deposition after 1-butene dehydrogenation at 600° C.

DETAILED DESCRIPTION OF THE PREFERRED EMBODIMENTS

Figure 1:
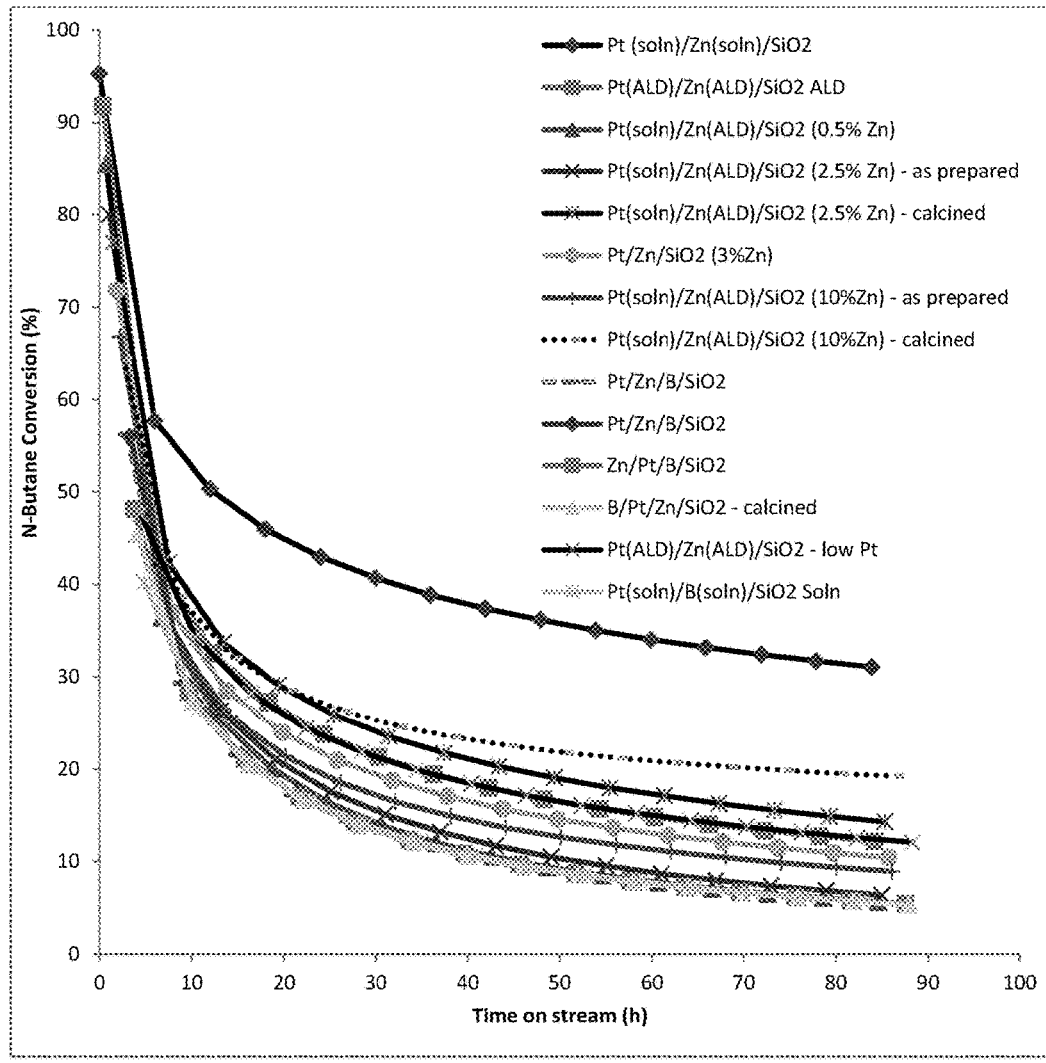
FIG. 1 shows experimental results for n-Butane conversion at 500° C. Experimental conditions: Catalysts: 10 mg diluted with 100 mg $SiO_2$; Pre-activation: The catalysts were pre-activated at 550° C. for 2 h using 10% $H_2$ in $N_2$; Catalysis Feed: 1% N-butane in Ar (100 mL/min)+He (16 mL/min) for 16 reactors; Reaction Temperature: 500° C.
Figure 2A:
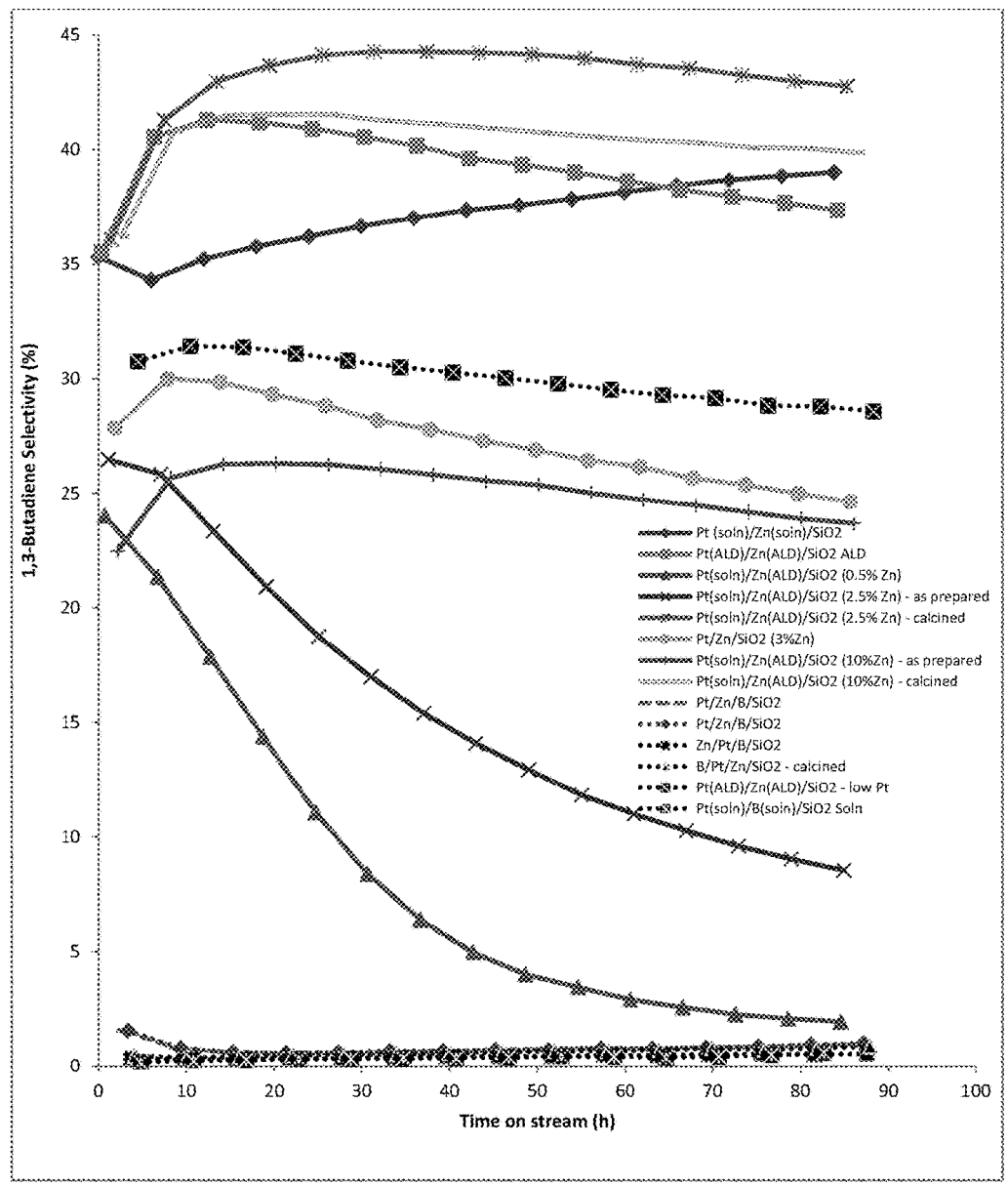
FIGS. 2A-2D show experimental results for catalyst selectivity to C4 alkenes and diene products.
Figure 2B:
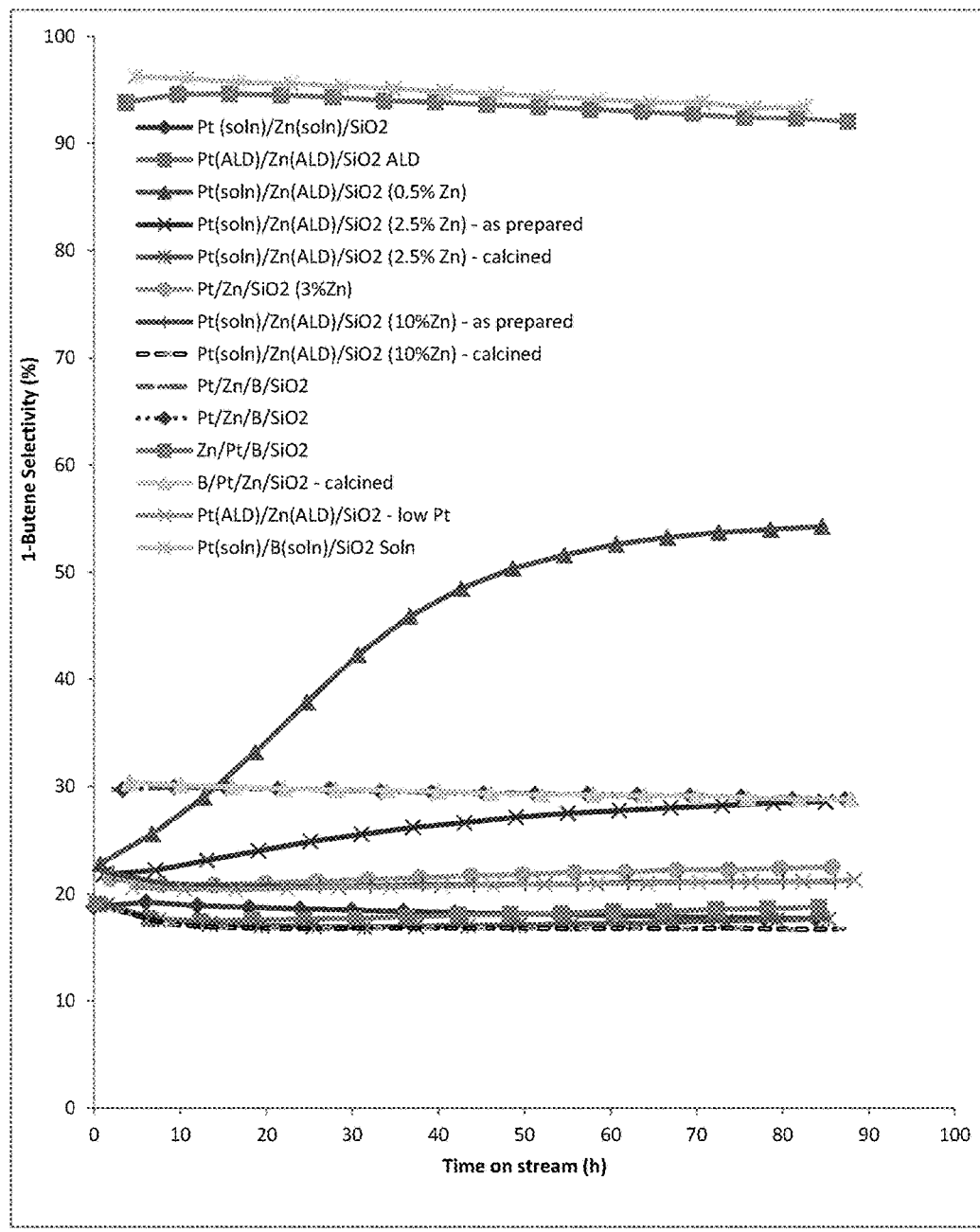
Figure 2C:
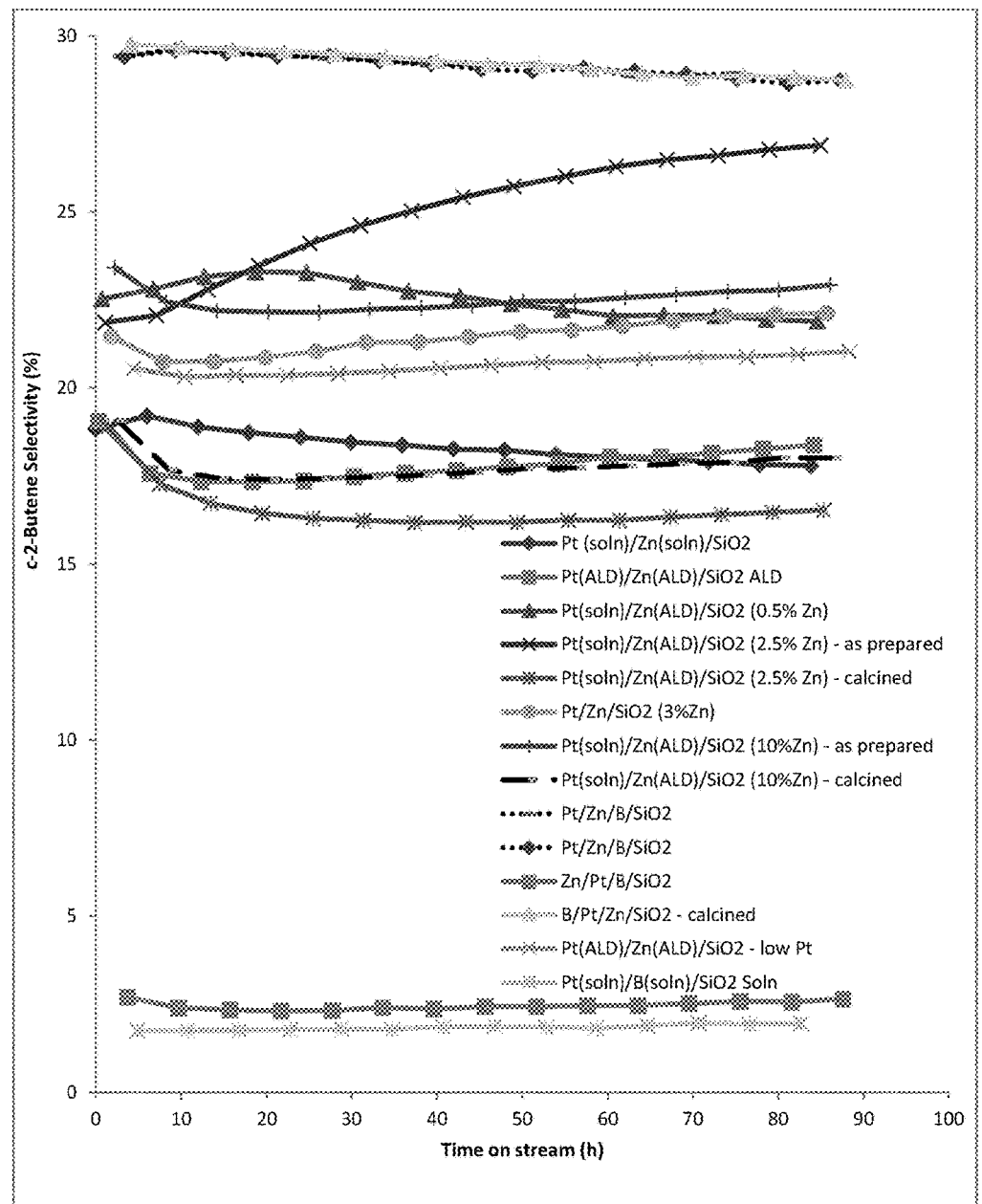
Figure 2D:
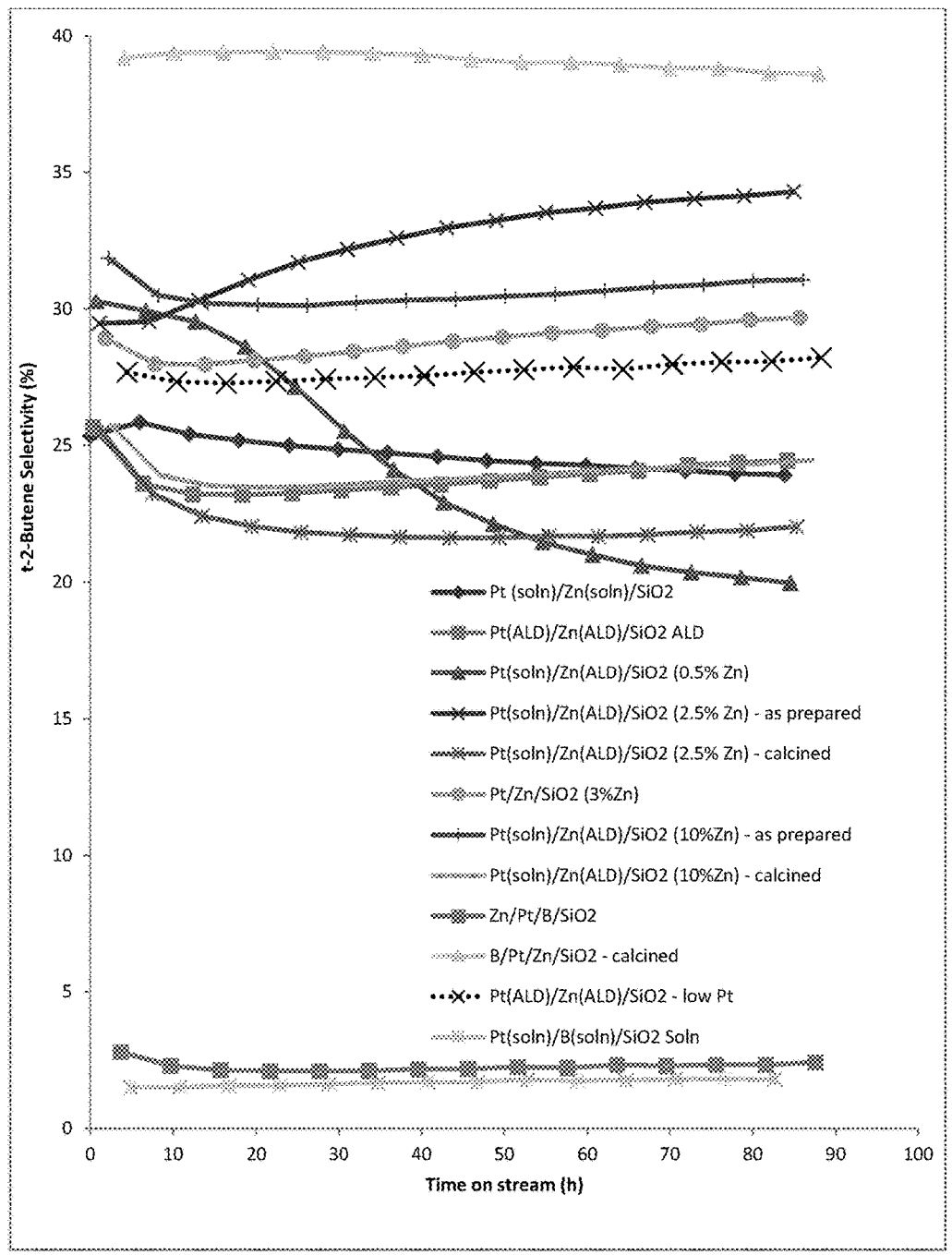

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present disclosure, as generally described herein, and illustrated in the figures, can be arranged, substituted, combined, and designed in a wide variety of different configurations, all of which are explicitly contemplated and made part of this disclosure.

Figure 12A:
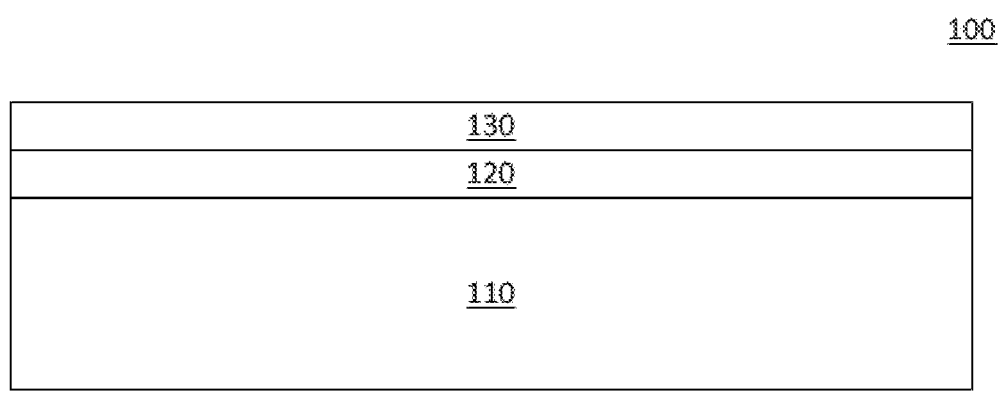
FIG. 12A illustrates an embodiment of a catalyst.
Figure 12B:
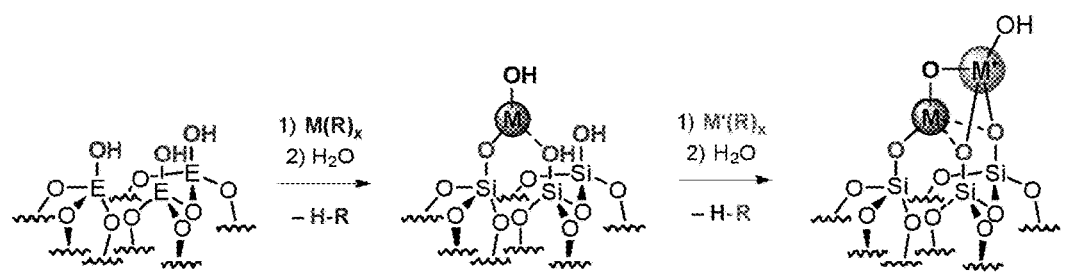
FIG. 12B illustrates a synthetic approach for one embodiment.
Figure 13:
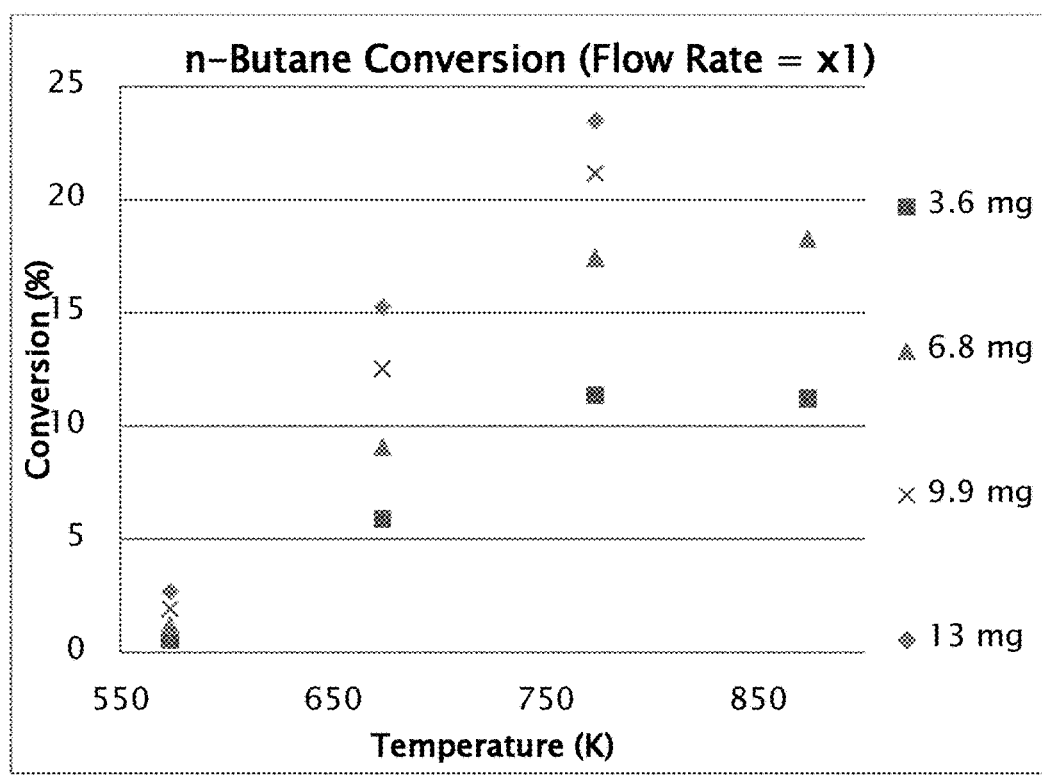
FIG. 13 illustrates conversion percentage for n-butane with different embodiments of catalyst loading.
Figure 14:
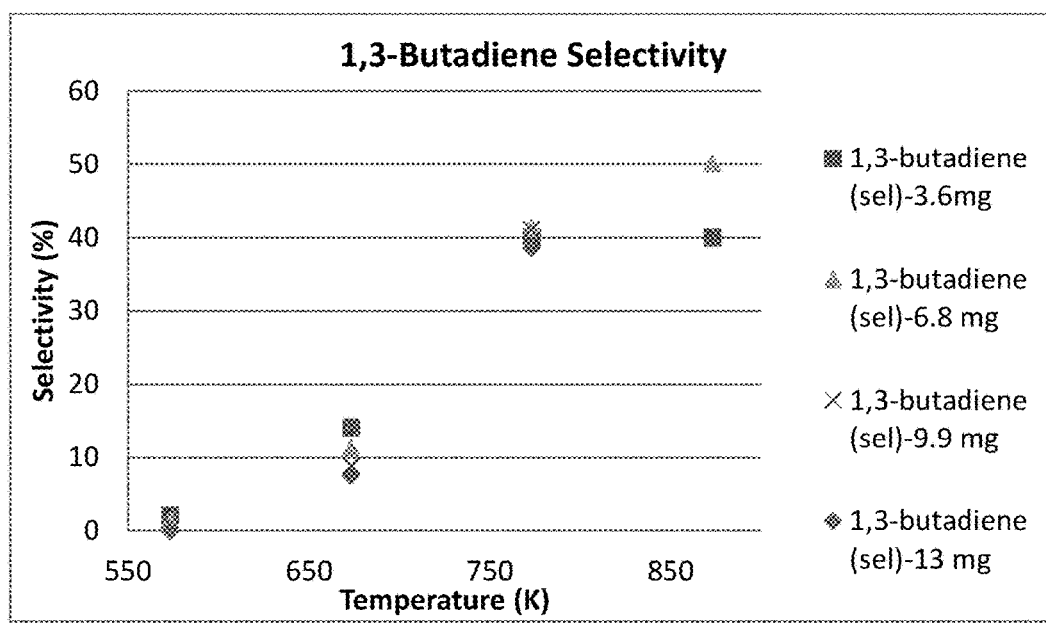
FIG. 14 illustrates selectivity for n-butane for 1,3 butadiene with different embodiments of catalyst loading.

FIG. 12A illustrates a simplified illustration of one embodiment of a catalyst 100 having a substrate surface 110, a metal layer 120 and a catalytic layer 130. FIG. 12B illustrates one embodiment of a general catalyst structure and a synthetic approach/strategy. Generally the catalyst 100 comprises M'/M/E$_x$O$_y$ where the catalyst M' is a Pt group metal, the promoter 120 is MO$_x$ (M being a transition metal (e.g., Zn or Fe) or a main group element material (e.g., Ga)) and E$_x$O$_y$ corresponds to a substrate surface 110 where E is Si, Al, Ti, or Zr (e.g., SiO$_2$ (silica) and/or Al$_2$O$_3$ (alumina)). While FIG. 12A illustrates the order of layers as substrate surface 110, promoter 120, catalytic layer 130, in some embodiments the promoter 120 and the catalytic layer 130 are interchanged (such as by being introduced to the substrate surface 110 simultaneously). FIG. 12B illustrates a general catalyst structure and a synthesis pathway for some embodiments. While the catalytic metal 130 and the promoter 120 are shown as a discrete layers, in some embodiments the catalytic metal 130 and/or the promoter 120 are each formed of isolated sites or extended structures such as clusters, islands, particles, or flakes. In some embodiments, the catalytic metal 130 and/or the promoter 120 each are a monolayer or submonolayer. In other embodiments, the catalytic metal 130 and/or the promoter 120 each may include multiple layers. In some embodiments, the catalytic metal 130 and/or the promoter 120 each may include at least 2 layers, at least 3 layers, at least 4 layers, at least 5 layers, and/or at least 10 layers. Further, although not illustrated in FIG. 12A or FIG. 12B, the catalyst 100 may be, in some embodiments, doped with Groups I (e.g. Li, Na, K), Group II (e.g., Mg and Ca), and main group elements (e.g., B and Sn). In a particular embodiment, catalysts with boron dopant are observed to suppress coking relative to catalysts without boron dopants.

The catalyst may facilitate high selectivity and conversion rate for dehydrogenation reactions when compared to known materials utilizing the catalytic layer on a silica substrate surface or the catalytic layer with other substrates such as alumina. In one embodiment the catalyst is made by thin film deposition techniques, including solution-phase synthesis (e.g., impregnation and surface organometallics) and gas-phase synthesis (e.g., atomic layer deposition), by depositing the metal layer 120 on the substrate surface 110.

The substrate surface comprises a support material with the general formula of $E_xO_y$ as stated above. In some embodiments, the support material is selected from an oxide substrate such as zirconia, titania, silica or alumina, or the like. Further, the substrate may comprise a substrate surface composed of any of the preceding. Prior attempts at using silica with platinum as a catalyst has resulted in poor performance including a short life-span due to fouling of the catalyst active sites. See, e.g., U.S. Pat. Nos. 4,005,985 and 4,041,099 describe silica-free dehydration reactors. In one embodiment, the silica substrate is a high surface area substrate and may be formed as a membrane, as a particle (e.g. a bead or powder), or as some other structure. The substrate surface 110 may be a porous body. In various embodiments the substrate surface 110 has a surface area, incrementally, of at least 1 m²/g, at least 5 m²/g, at least 10 m²/g, at least 20 m²/g, at least 40 m²/g, at least 60 m²/g, at least 80 m²/g, and/or at least 100 m²/g. In some embodiments, the substrate surface 110 has a surface area, incrementally, of up to about 10000 m²/g, up to 5000 m²/g, up to 1000 m²/g, up to 500 m²/g, up to 250 m²/g, up to 150 m²/g, up to 120 m²/g, up to 100 m²/g, up to 80 m²/g, and/or up to 60 m²/g. In other embodiments, substrate surface 110 may have a surface area of more than 10,000 m²/g or less than 1 m²/g. The supports may be microporous, mesoporous, or macroporous in various embodiments. The particles of alumina/silica may be, in one embodiment, of any size appropriate for the scale of the structure.

In one embodiment the promoter 120 comprises an oxide layer of a transition metal or a main group element. The application of metal oxide promoters improves catalyst stability as evidenced by slower catalyst deactivation. In particular embodiments, the transition metal oxide promoter 120 has the general formal $MO_x$ where M=a transition metal or main group metal, specifically $MO_x$ may include but is not limited to $TiO_2$, $ZrO_2$, $CoO_x$ (x=1-1.5), ZnO, $MnO_x$ (x=1 to 4), $Al_2O_3$, $Ga_2O_3$. Further, the transition metal is, in certain embodiments, a first row transition metal. The metal layer 120 has a thickness. In one embodiment the promoter may be such that it does not provide complete coverage of the silica substrate 110. For example, the promoter 120 may be deposited by a thin film deposition technique provide for less than complete loading on the substrate surface 110 forming a partial mono-layer. In another embodiment a complete monolayer of the promoter 120 is formed. In yet another embodiment the promoter 120 may include at least 2 layers, at least 3 layers, at least 4 layers, at least 5 layers, and/or at least 10 layers.

The catalytic metal 130 includes a catalytic material including, but are not limited to, platinum and platinum group metals. In one embodiment the catalytic metal 130 consists essentially of platinum. In another embodiment, the catalytic metal 130 consists of platinum containing material. The types of Pt and distribution of Pt sites (isolated vs clusters vs particles) vary depending on the synthesis method. It is believed that there is advantage for when the metals are installed by ALD compared to solution-phase synthesis methods. For example, ALD gives more isolated sites than solution-phase synthesis.

Further the catalytic metal 130 may include a dopant. In some embodiments, a dopant is applied on top of the active catalyst: $M/M'/E_xO_y$ (e.g. $Zn/Pt/SiO_2$). In yet other embodiments, two or more different dopants are applied on top of the active catalyst: $M/M'/E_xO_y$ (e.g., $Zn/Pt/B/SiO_2$; in this case, the sequence of deposition is: (1) B, (2) Pt and (3) Zn); the boron dopant is an under layer while the ZnO is an overcoat. Dopants may include various cations such as $Zn^{2+}$ or $B^{3+}$, and further such as Group 13 cations, Group 1 cations, and Group 2 cations. Thus, in the final composition the dopant layer may be an oxide of such materials, for example $B_2O_3$ or ZnO. Unless otherwise indicated, the descriptions of the catalyst materials herein shall use a short-hand nomenclature referring to the deposited element rather than the cation form.

Each of the substrate surface 110, promoter 120 and catalyst 130 may be essentially pure such that at least 90% and/or at least 95% of each individual layer is formed from a common type of material.

The catalyst provides a general synthetic approach to silica-based multimetallic catalysts for butane dehydrogenation with improved stability and selectivity. In one embodiment the general pathway catalyzed by the catalyst 100 is:

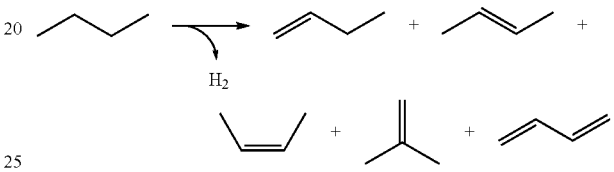

In one embodiment the catalytic metal 130 is surface exposed, meaning there is no overcoat deposited on the catalytic metal 130. It is believe this is due to the lower concentration of exposed catalyst (Pt) sites. However, the use of an overcoat has been observed to increase stability (against active site sintering). In one embodiment, an overcoat, such as alumina, can be utilized as the promoter, both acting as a promoter and to stabilize active catalyst sites thereby improving stability.

In addition, while some prior art references have stressed the use of multiple metal oxides as promoters 120, in one embodiment the promoter 120 consists essentially of a single metal oxide, preferably zinc oxide.

Catalysis described herein may be used in a range of temperatures. In one embodiment, the range of temperatures for catalyzing a butane dehydrogenation reaction is 400° C. to 800° C., 400° C. to 600° C., 400° C. to 500° C., 500° C. to 600° C., 450° C. to 550° C. and 475° C. to 525° C. In one embodiment, a $Pt/ZnO/SiO_2$ is stable above 600° C. In one embodiment, a $Pt/ZnO/B_2O_3/SiO_2$ is stable above 600° C.

Catalysis described herein exhibit a selectivity of at least 80%, at least 90%, at least 92%, at least 94%, at least 95%, at least 96%, at least 98%, at least 99%, or at least 99.5%. In one embodiment the selectivity is to a material selected from 1,3, butadiene, butenes (generally), 1-butene, c-2-butene, t-2-butene. In one embodiment, the catalyst is applicable for 1-butene dehydrogenation and for n-butane dehydrogenation. In one embodiment, a selectivity of at least 10%, 20%, 30%, 40%, 50%, 60%, 70% or a range of 10-70% to 1,3, butadiene is observed with a $Pt/MO_x/SiO_2$ catalyst. In one embodiment, a selectivity of at least 10%, 20%, 30%, 40%, 50%, 60%, 70% to butenes is observed with a $Pt/MO_x/SiO_2$ catalyst. Catalysis exhibit a conversion of at least 50%, at least 55%, at least 60%, at least 65%, at least 70%, or at least 75%. In one embodiment the selectivity is observed after at least 10, at least 20, at least 30, at least 40, at least 50, at least 60, at least 70 hours, or at least 90 hours without catalyst regeneration. In one embodiment the catalyst system comprises $Pt/Zn/SiO_2$ selective to 1, 3 butadiene, in another $Pt/B/SiO_2$ selective to butenes.

FIG. 12B illustrates an example synthesis method for an embodiment having MOx as the promoter and Pt as the catalytic metal. In general, the promoter is deposited on the silica oxide substrate and the catalytic metal is deposited on the promoter.

Various synthesis methods may be used for depositing the platinum group metal, the transition metal and the silica. For example, synthesis methods may include thin-film deposition techniques, such as but not limited to Atomic Layer Deposition (ALD), solution processes (Sol'n) or strong electrostatic adsorption (SEA). In many exemplary embodiments, one or more of the catalytic metal 130, the promoter 120 and the substrate surface 110 can be form by atomic layer deposition (ALD). ALD utilizes alternating exposures between precursors (e.g. in a gaseous form) and a solid surface to deposit materials in a monolayer-by-monolayer fashion. This process can provide uniformity of the coatings in many embodiments, including on nanoporous substrate materials. A catalyst system may be manufactured using a combination of deposition methods. Further, the number of cycles for each deposition may be varied, for example the number of ALD cycles. In many embodiments, this process also allows good control over the thickness and composition of the coatings. One embodiment utilized ALD for deposition of both the Pt and ZnO, another embodiment utilized ALD for ZnO but used a solution-phase process for deposition of the platinum and a third embodiment used SEA for ZnO and solution-phase for platinum. The types of Pt and distribution of Pt sites (isolated vs clusters vs particles) vary depending on the synthesis method. It is believed that for some embodiments, there is an advantage for when the metals are installed by ALD compared to solution-phase synthesis methods. It has been observed that the Pt to promoter ratio has a larger impact on catalytic activity than the deposition methods used.

The thickness of the layers may be varied. In one embodiment the promoter has a mono layer or submono layer thickness.

Experiments n-Butane Dehydrogenation

Variable Temperature Dehydrogenation and Catalyst Stability Studies

With reference to FIG. 5A through 9D, experiments were carried out to study the impact of temperature on n-butane conversion rate and catalyst thermal stability. In a first set of experiments, temperature was varied for each of four catalysts: Pt/Zn/SiO$_2$ fabricated by solution-phase synthesis "Sol'n"; Pt/Zn/SiO$_2$ fabricated by ALD; Pt/Zn/B/SiO$_2$ (i.e., boron-doped) fabricated by ALD; and Pt/B/SiO$_2$ fabricated by Sol'n. Experiments were run at 450° C., 500° C., 550° C., or 600° C. for each of those four catalysts.

The boron-doped catalysts exhibit stability at 600° C. FIGS. 6-9 show the selectivity of each catalyst to the four C4 products (1,3-butadiene, 1-butene, cis-2-butene and trans-2-butene) at each reaction temperature (450, 500, 550 and 600° C.).

Selectivity Profiles

Experiments were performed to determine selectivity for 1,3 butadiene for four catalysts: Pt/Zn/SiO$_2$ fabricated by Soln; Pt/Zn/SiO$_2$ fabricated by ALD; Pt/Zn/B/SiO$_2$ (i.e., boron-doped) fabricated by ALD; and Pt/B/SiO$_2$ fabricated by Soln. FIGS. 6A-6D illustrate the results. Both the Soln and ALD versions of a Pt/Zn/SiO2 catalyst exhibited superior selectivity. Further, both of those Pt—Zn catalysts exhibited high levels of stability at 450° C. and 500° C. See FIGS. 6A-6D Pt/Zn/SiO$_2$ (solution-phase) and Pt/Zn/SiO$_2$ (ALD) both exhibit the highest activity and selectivity (among the catalyst tested) to 1,3-butadiene formation. Pt/Zn/B/SiO$_2$ is also selective to 1,3-butadiene. This catalyst is most notable for suppressed coke deposition. Pt/B/SiO$_2$ shows low selectivity to 1,3-butadiene, giving butenes as the main dehydrogenation products. Coke-formation is also suppressed using this catalyst.

For those same four catalysts, experiments were performed to determine selectivity for butenes (1-butene, c-2-butene, and t-2 butene). FIG. 6A-6D illustrate the results. The Pt/B/SiO$_2$ exhibited pronounced selectivity to 1-butene at 500° C. and higher.

Selectivity for 1-butene was also studied for those same four catalysts. FIGS. 7A-7D illustrate the results. The Pt/B/SiO$_2$ catalyst shows the highest selectivity to 1-butene. Notably, the selectivity is similar at the lowest temperature and the boron-doped catalyst increases by a factor of two in selectivity at the higher three temperatures in comparison.

Selectivity for cis-2-butene was also studied for those same four catalysts. FIGS. 8A-8D illustrate the results. The Pt—Zn catalyst show the highest selectivity. The zinc-promoted Pt catalysts show higher selectivity to cis-2-butene (indication of its strong tendency to isomerize olefins)

Selectivity for trans-2-butene was also studied for those same four catalysts. FIGS. 9A-9D illustrate the results. The Pt—Zn catalyst show the highest selectivity. The results are very similar to the cis-2-butene results.

The selectivity and dehydrogenation activity was also studied for the four catalysts Pt/Zn/SiO$_2$ fabricated by Soln; Pt/Zn/SiO$_2$ fabricated by ALD; Pt/Zn/B/SiO$_2$ (i.e., boron-doped) fabricated by ALD; and Pt/B/SiO$_2$ fabricated by Soln. A study by temperature is shown in FIGS. 12A-15B. FIGS. 16A-19B illustrate catalyst activity and stability by catalyst for 1,3 butadiene and butane production, respectively.

N-Butane Dehydrogenation Conclusions

Conversions as high as 70% with dehydrogenation to 1,3 butadiene of 60% were observed. The catalyst remained active over a 90 hour period. The selectivity between butenes and 1,3-butadiene can be tuned through the use of dopants. Boron-doped catalysts show an enhanced selectivity to monodehydrogenated products such as butenes. Boron promoters suppresses coke formation.

1-Butene Dehydrogenation

Figure 3:
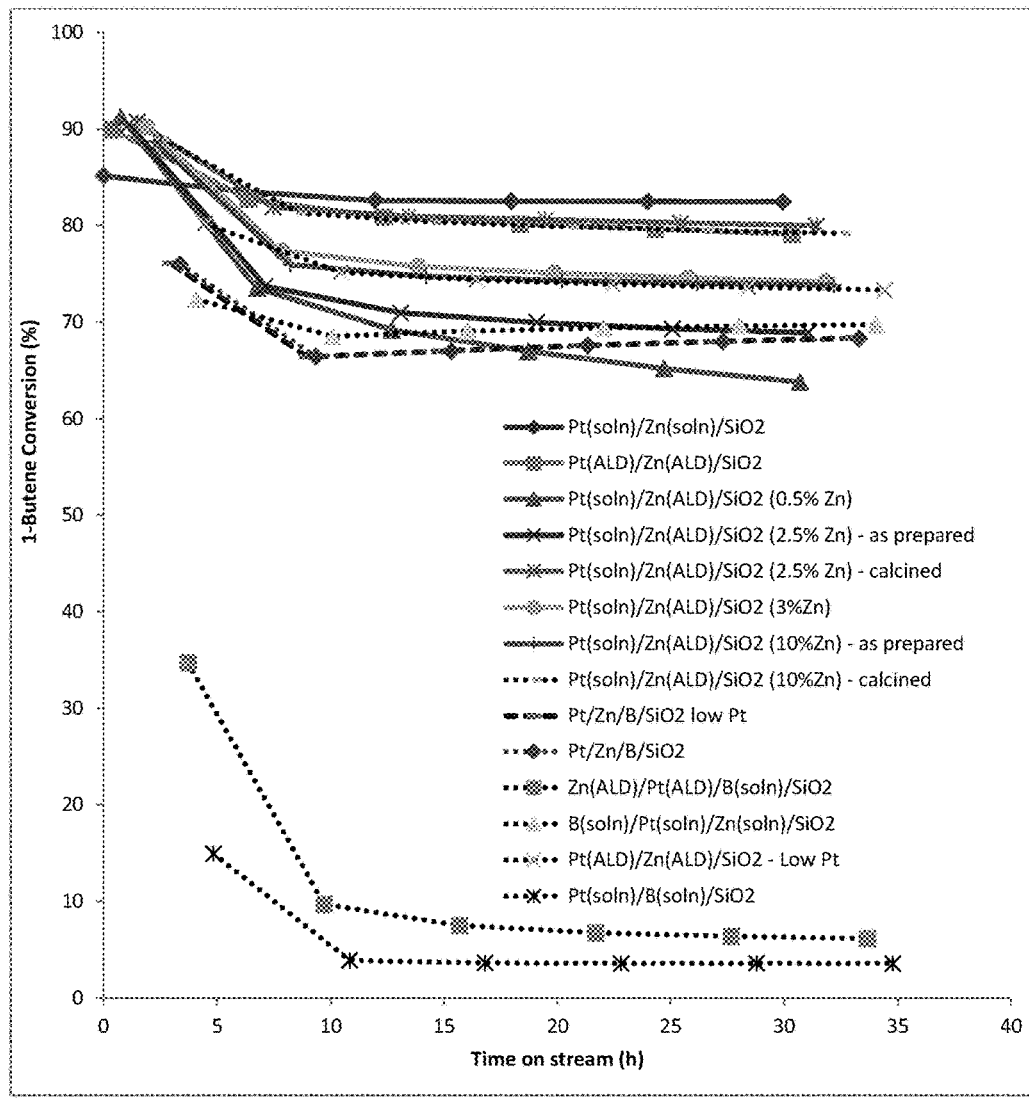
FIG. 3 shows experimental results for 1-Butene conversion at 500° C. Experimental conditions: Catalysts: 10 mg diluted with 100 mg $SiO_2$; Pre-activation: The catalysts were preactivated at 550° C. for 2 h using 10% $H_2$ in $N_2$; Catalysis Feed: 1% N-butane in Ar (100 mL/min)+He (16 mL/min) for 16 reactors; Reaction Temperature: 500° C.
Figure 4A:
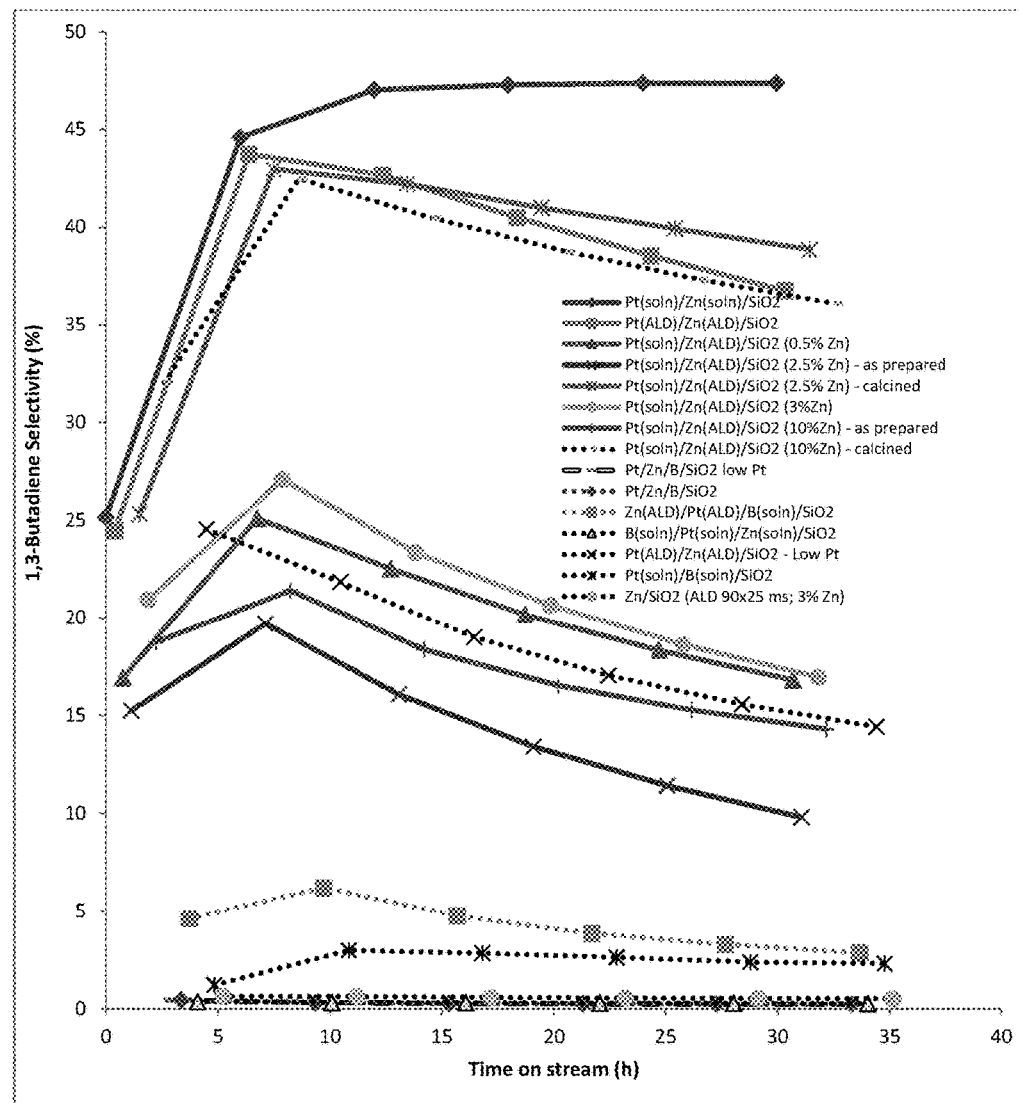
FIGS. 4A-4C show experimental results for catalyst selectivity to C4 alkene and diene products.
Figure 4B:
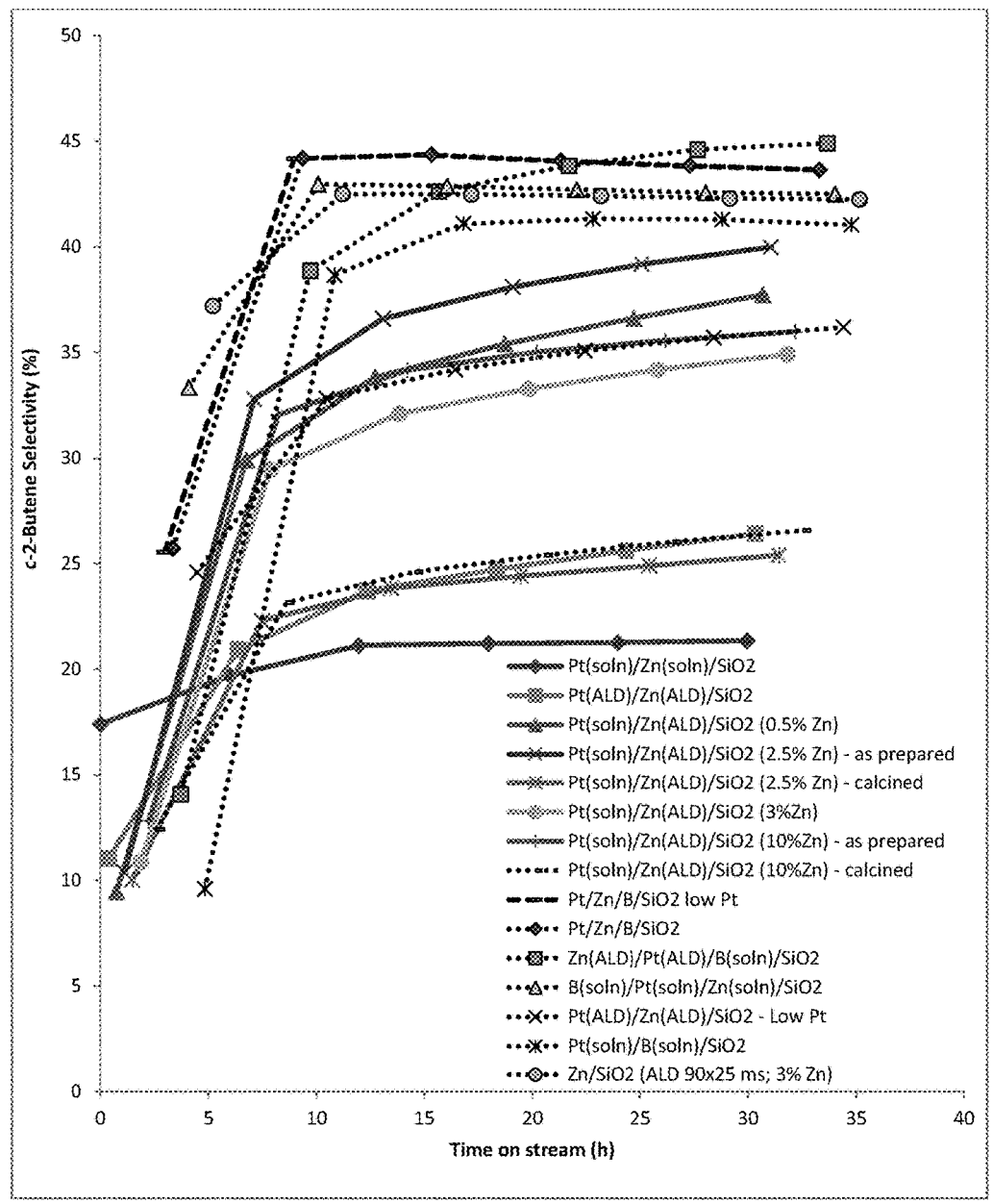
Figure 4C:
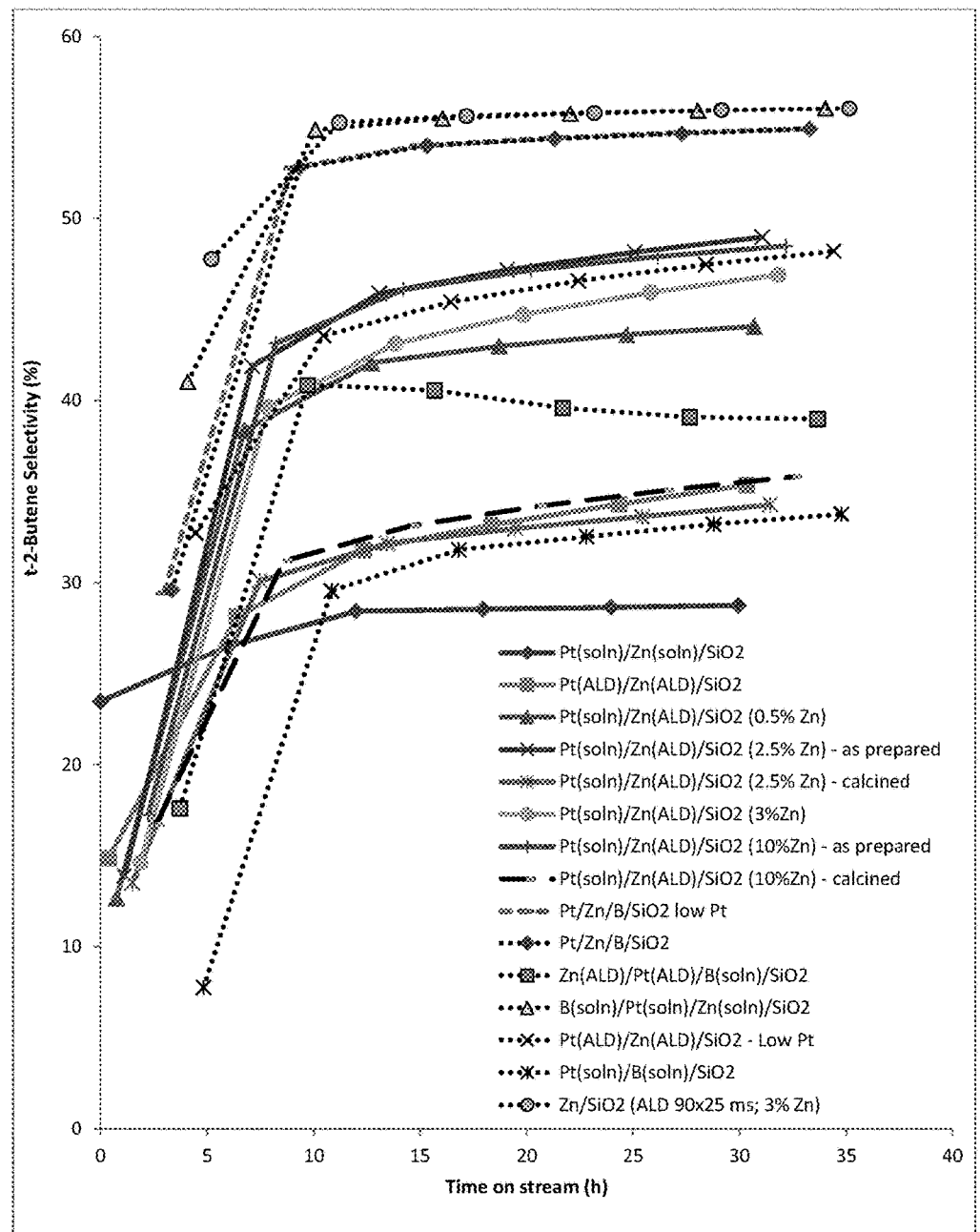
Figure 5A:
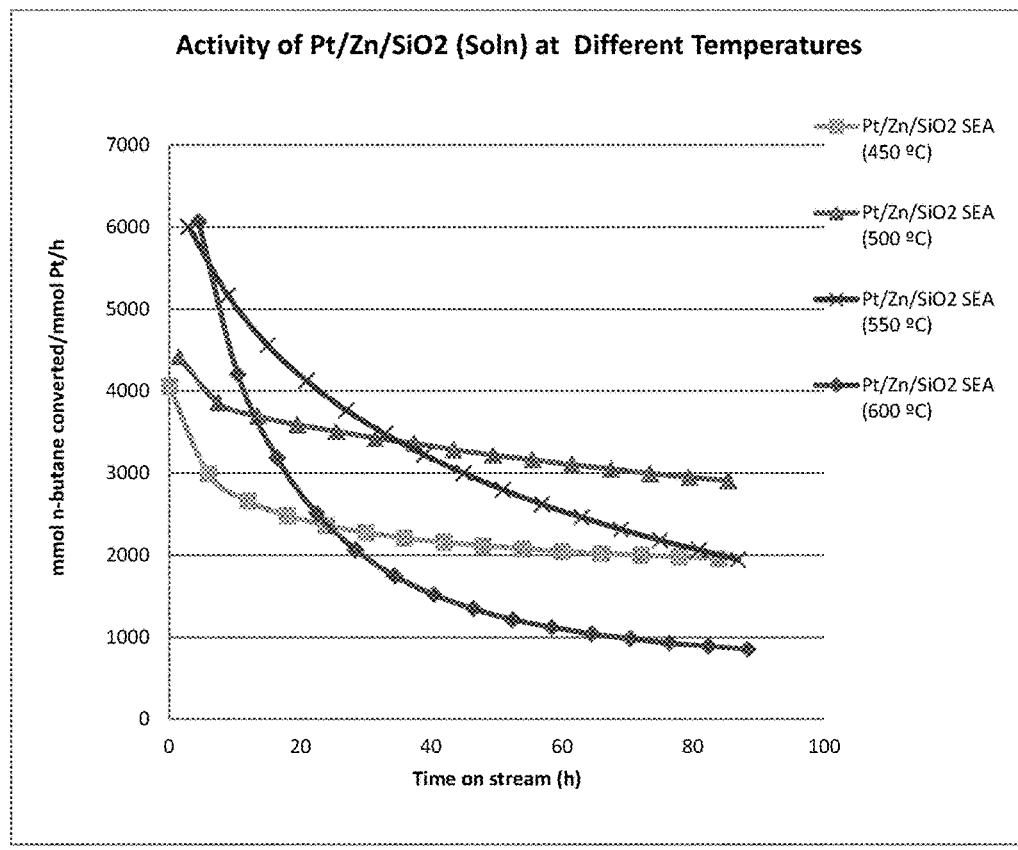
FIGS. 5A-5D show experimental results for n-Butane dehydrogenation for different catalyst synthesis methods.
Figure 5B:
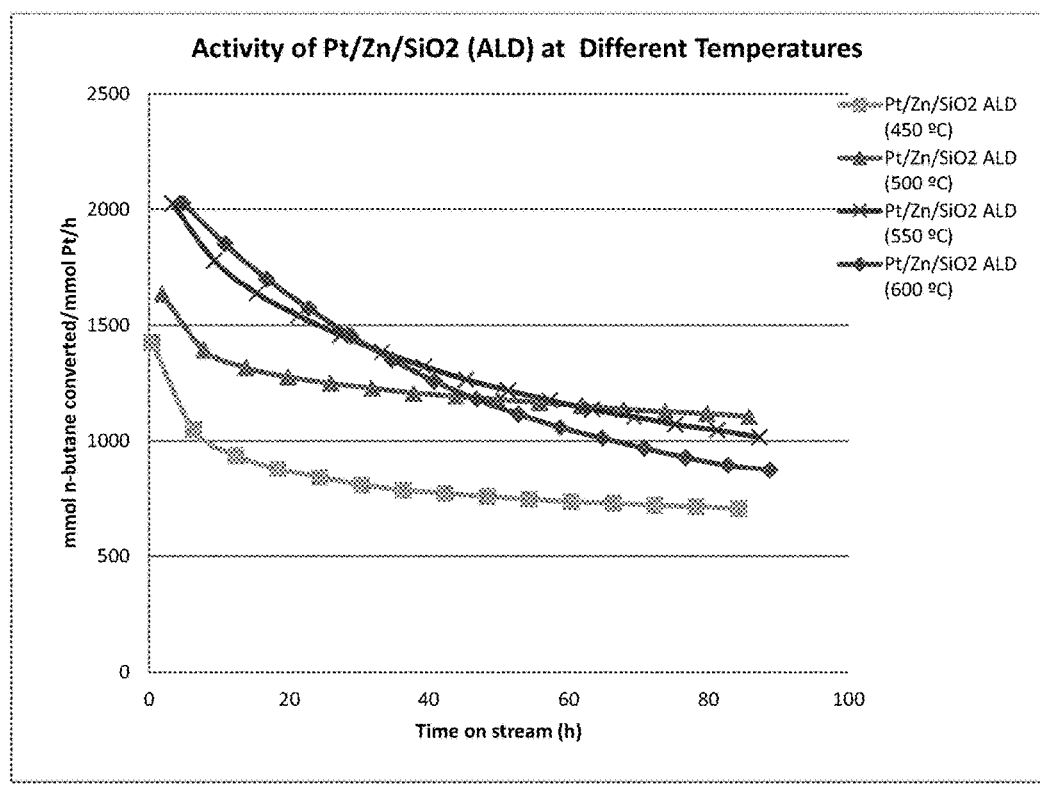
Figure 5C:
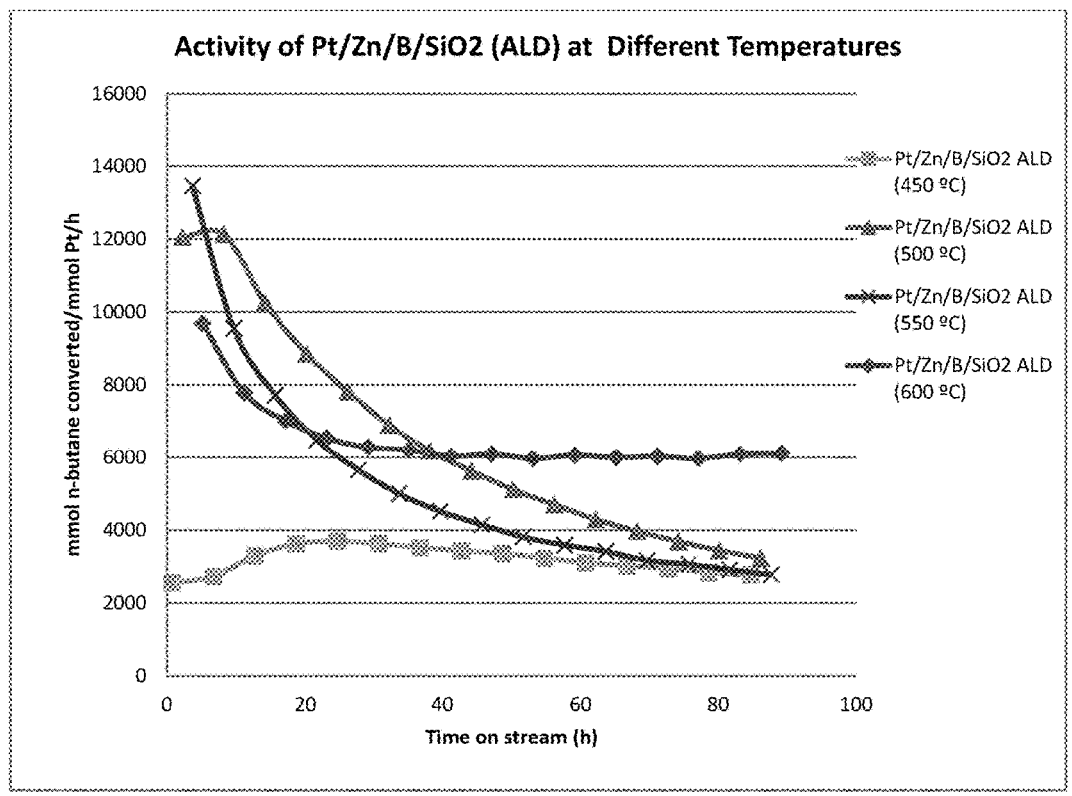
Figure 5D:
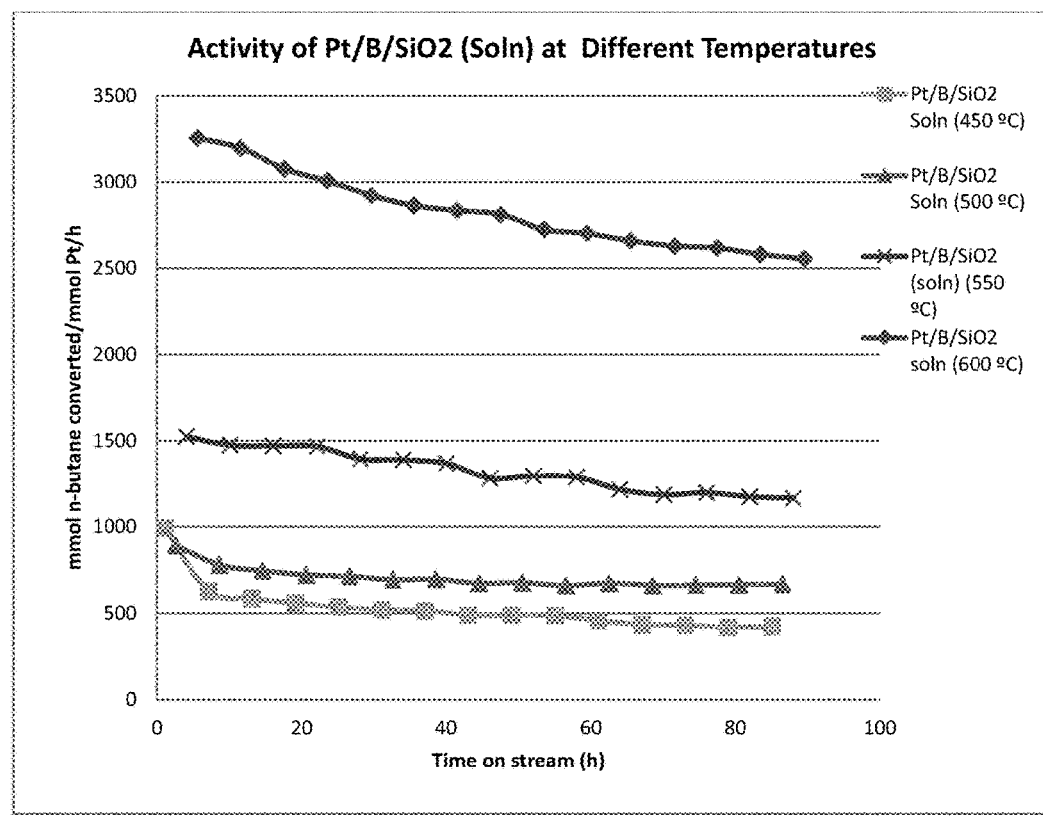
Figure 6A:
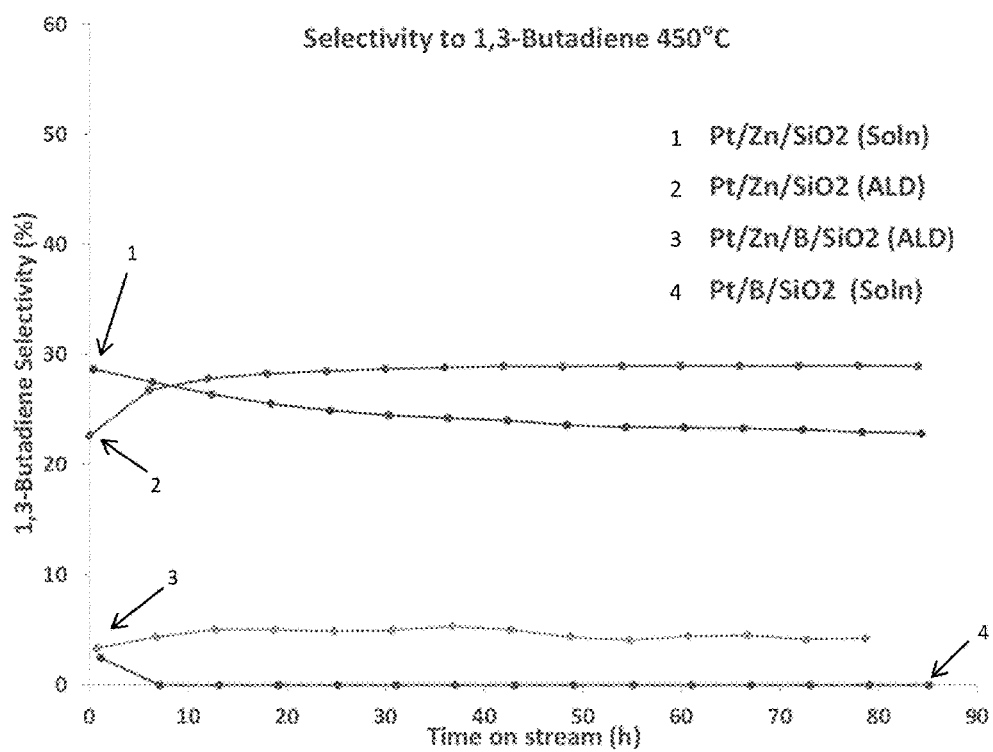
FIGS. 6A-6D show experimental results for different temperatures of selectivity to 1,3 butadiene from n-butane.
Figure 6B:
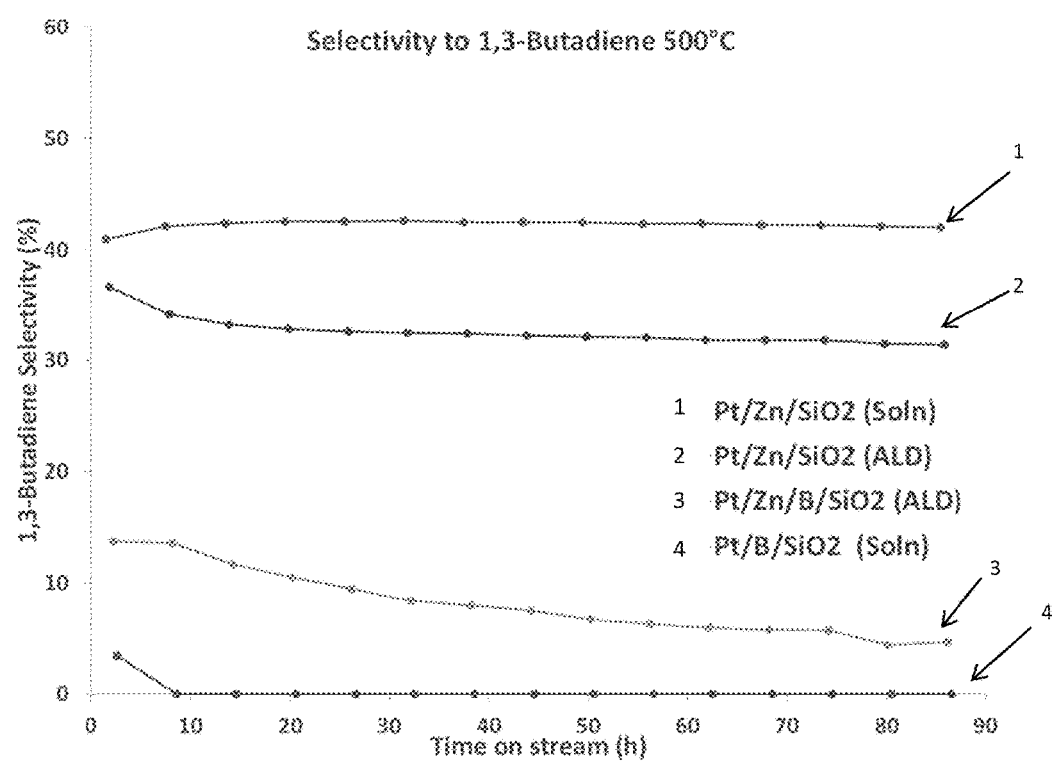
Figure 6C:
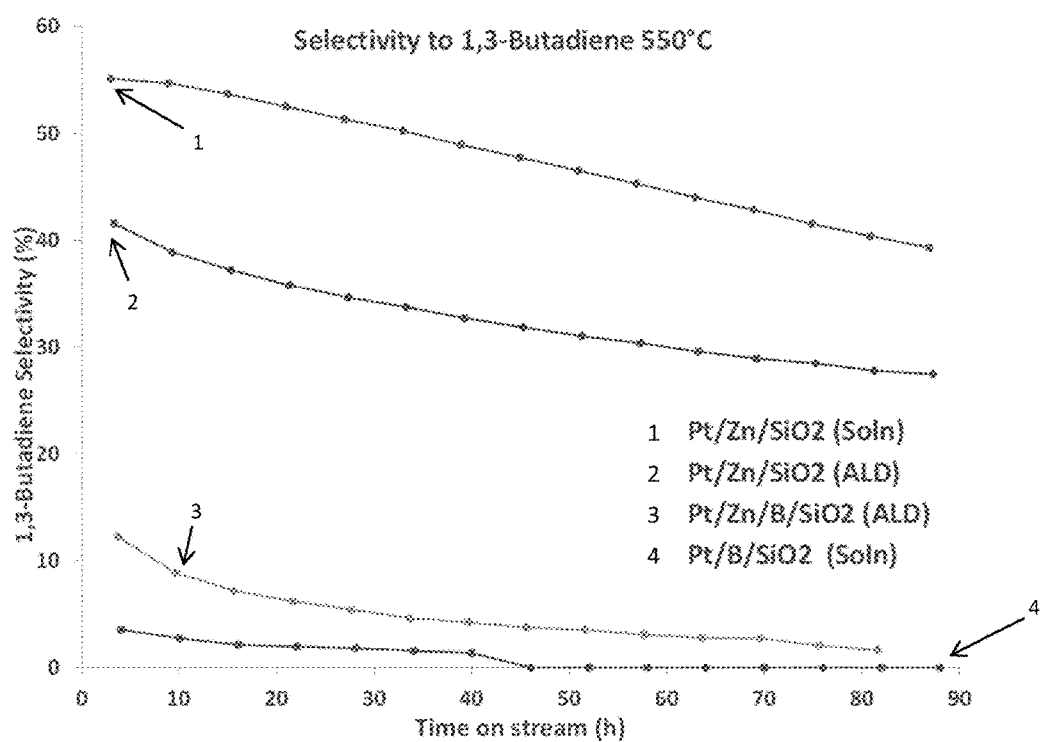
Figure 6D:
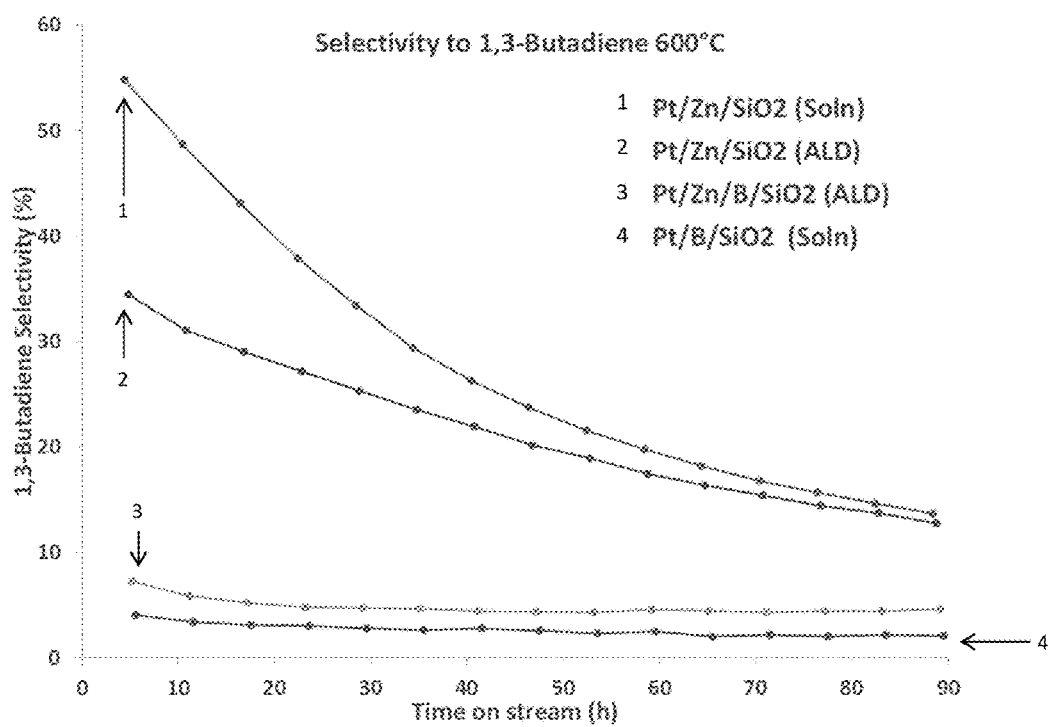
Figure 7A:
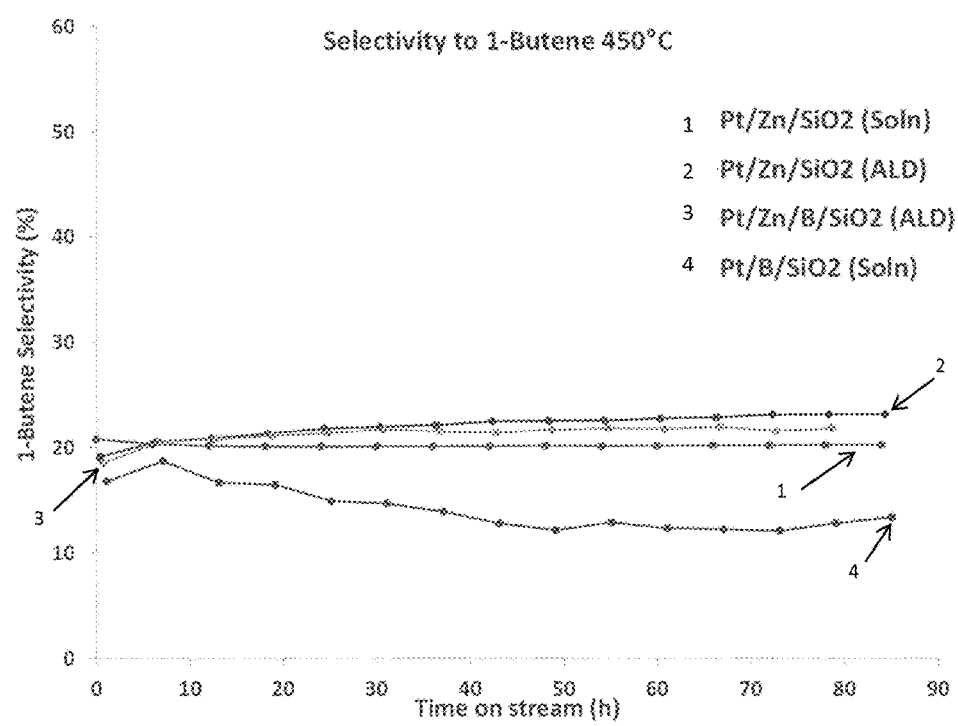
FIGS. 7A-7D show experimental results for different temperatures for selectivity to 1-butene from n-butane
Figure 7B:
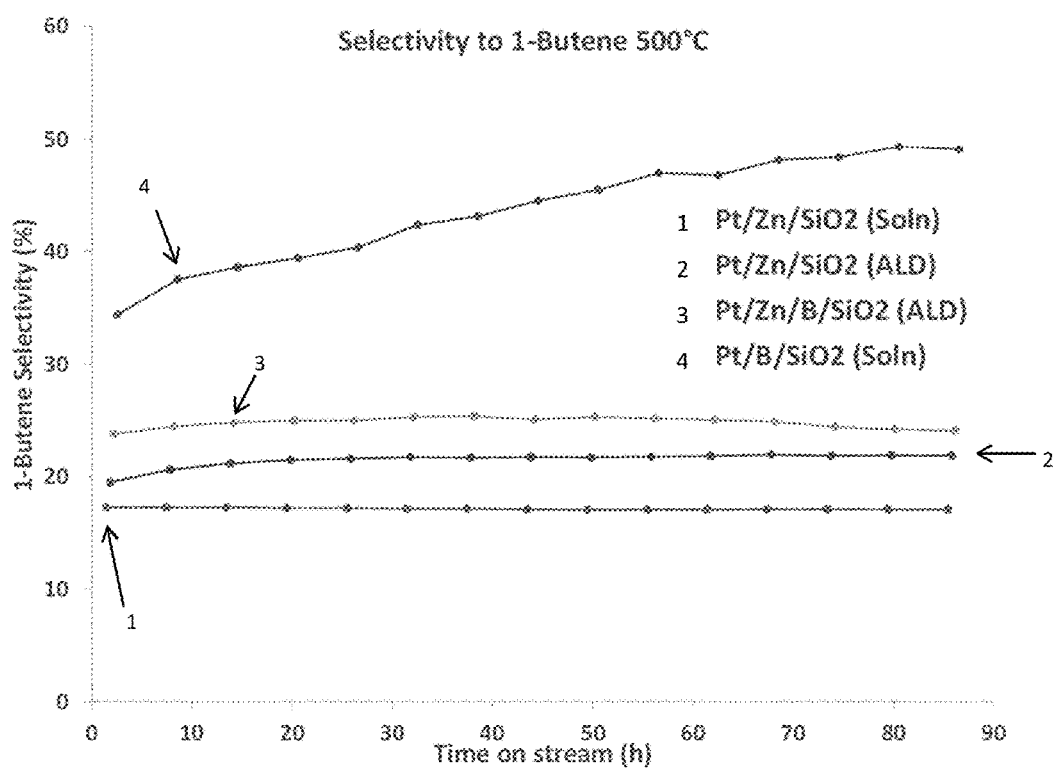
Figure 7C:
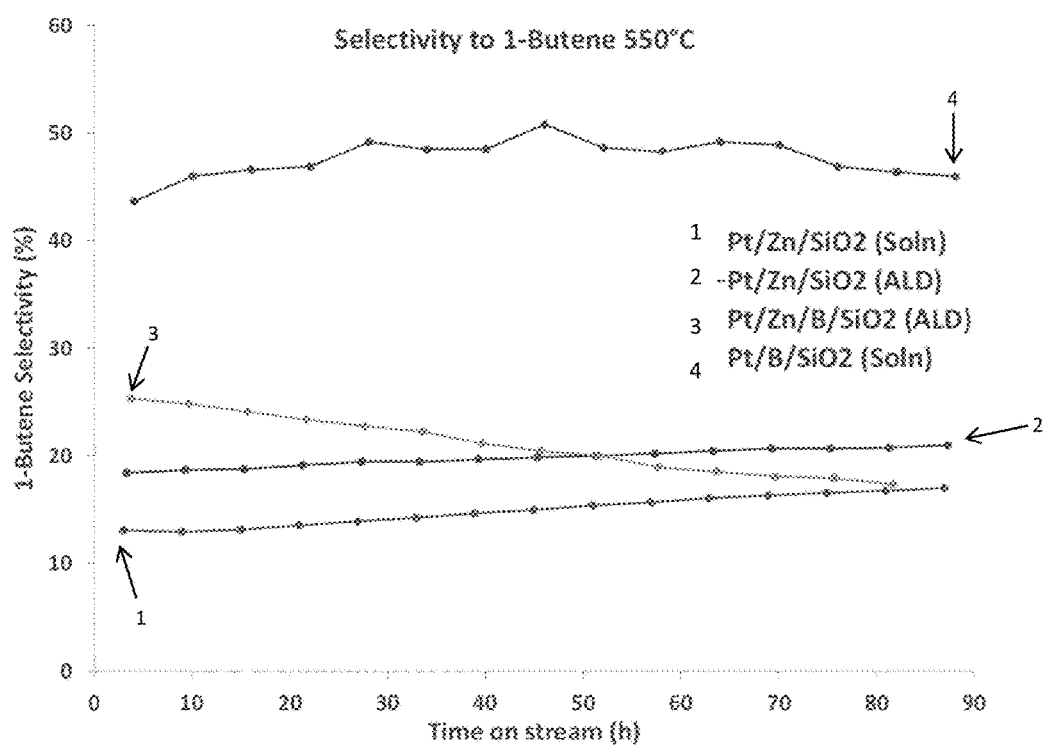
Figure 7D:
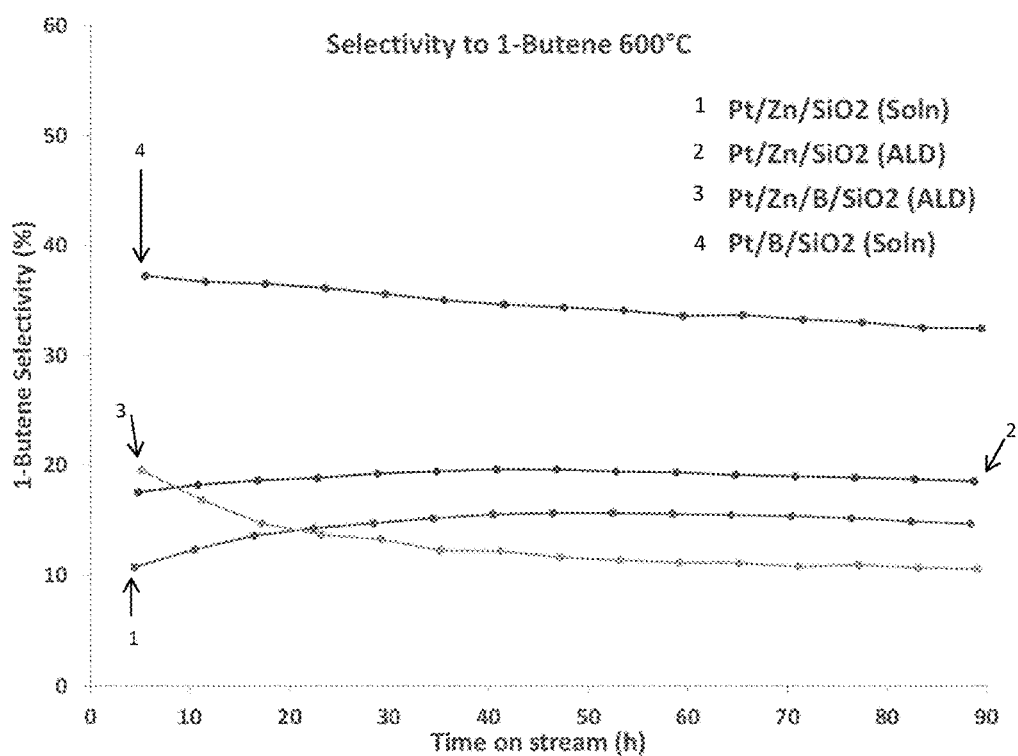
Figure 8A:
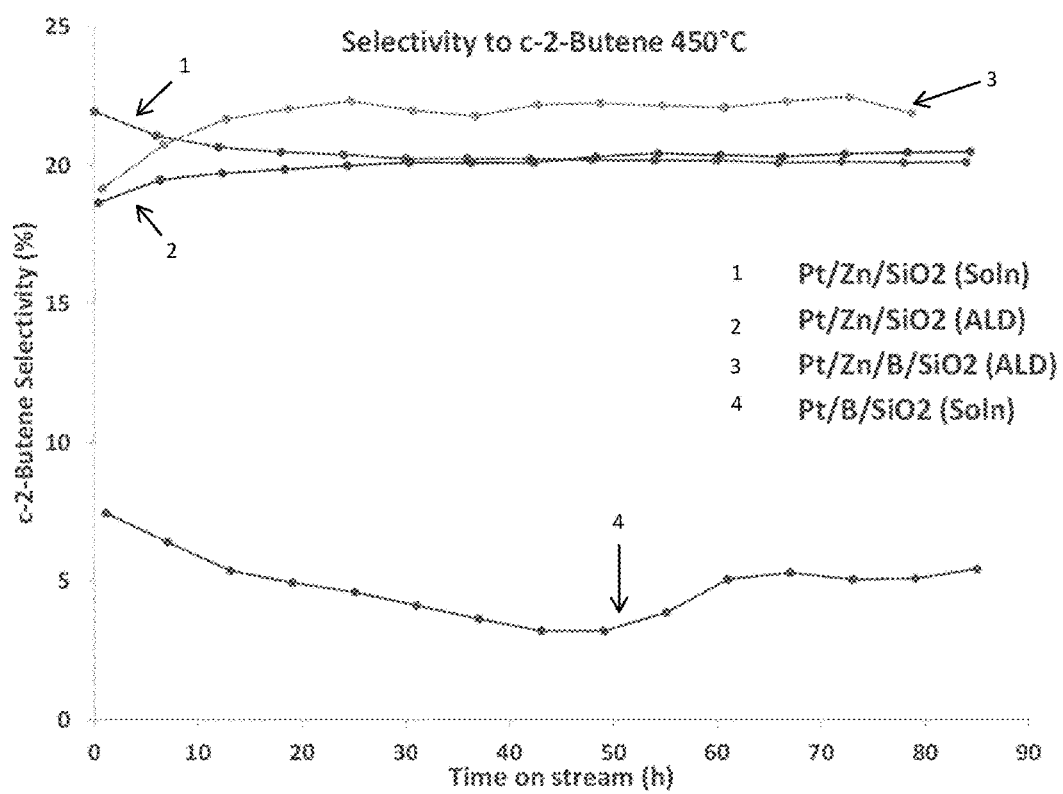
FIGS. 8A-8D show experimental results for different temperatures for selectivity to –2-butene from n-butane.
Figure 8B:
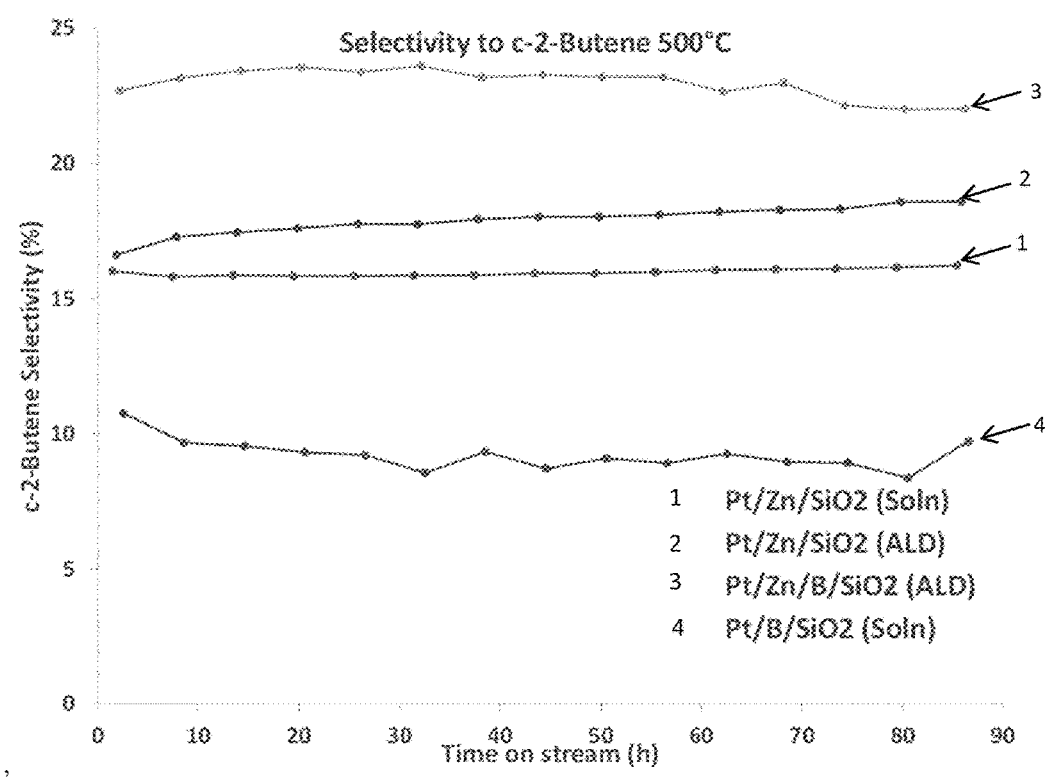
Figure 8C:
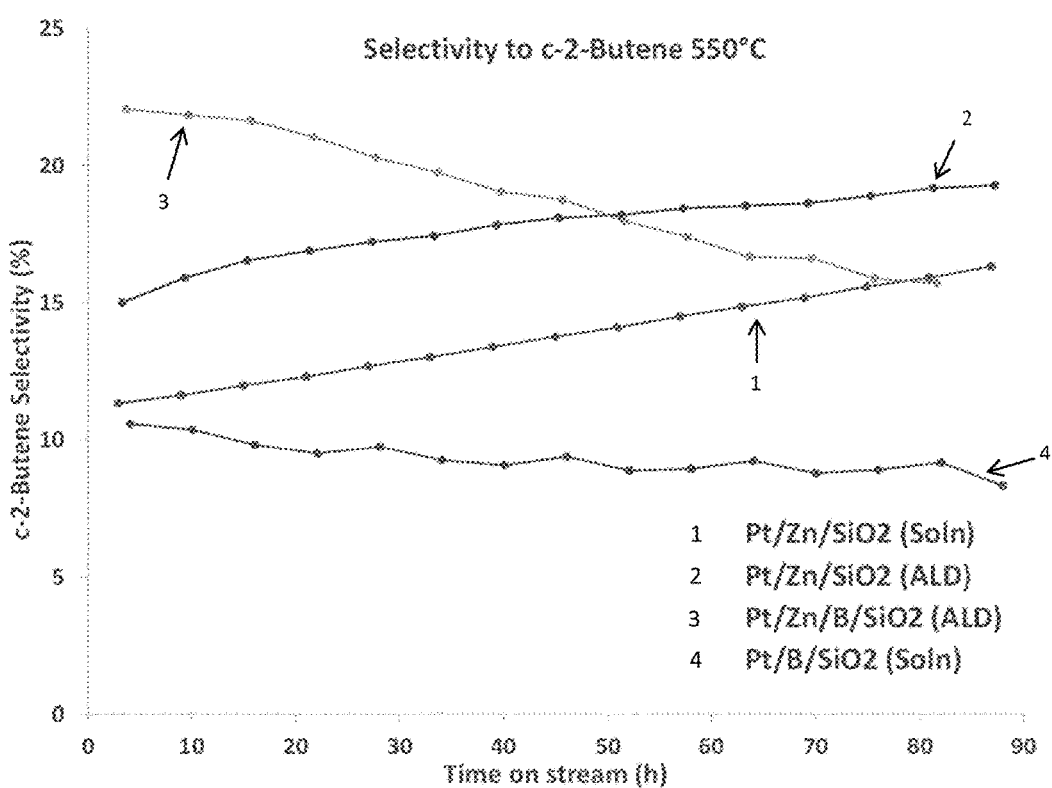
Figure 8D:
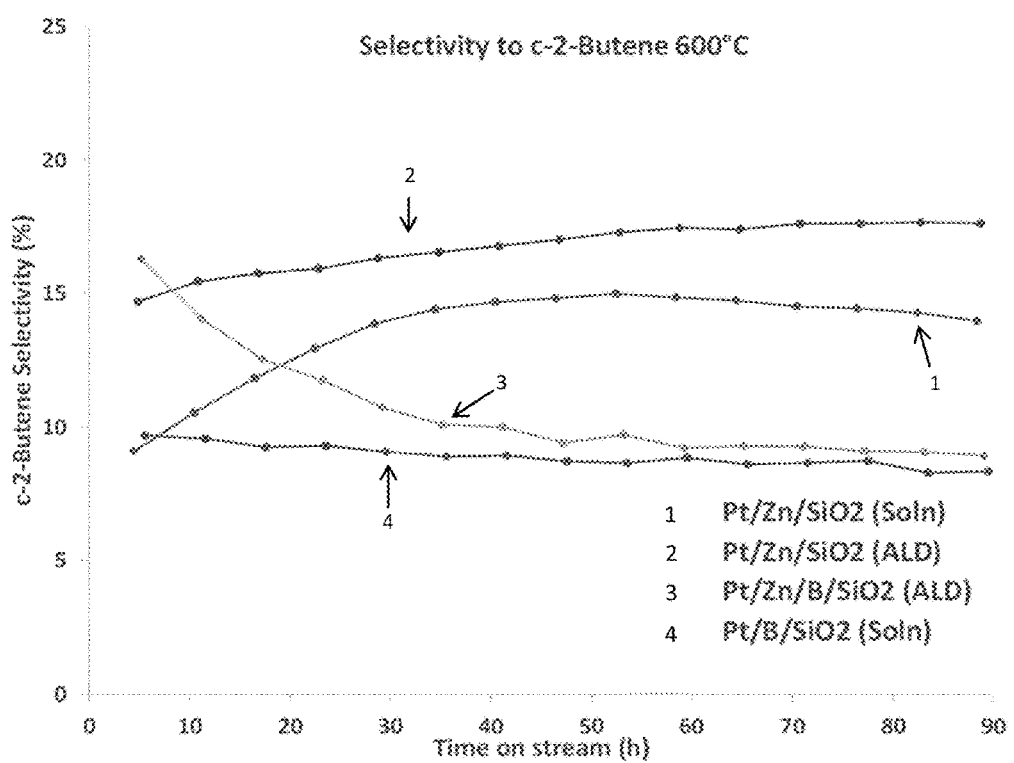
Figure 9A:
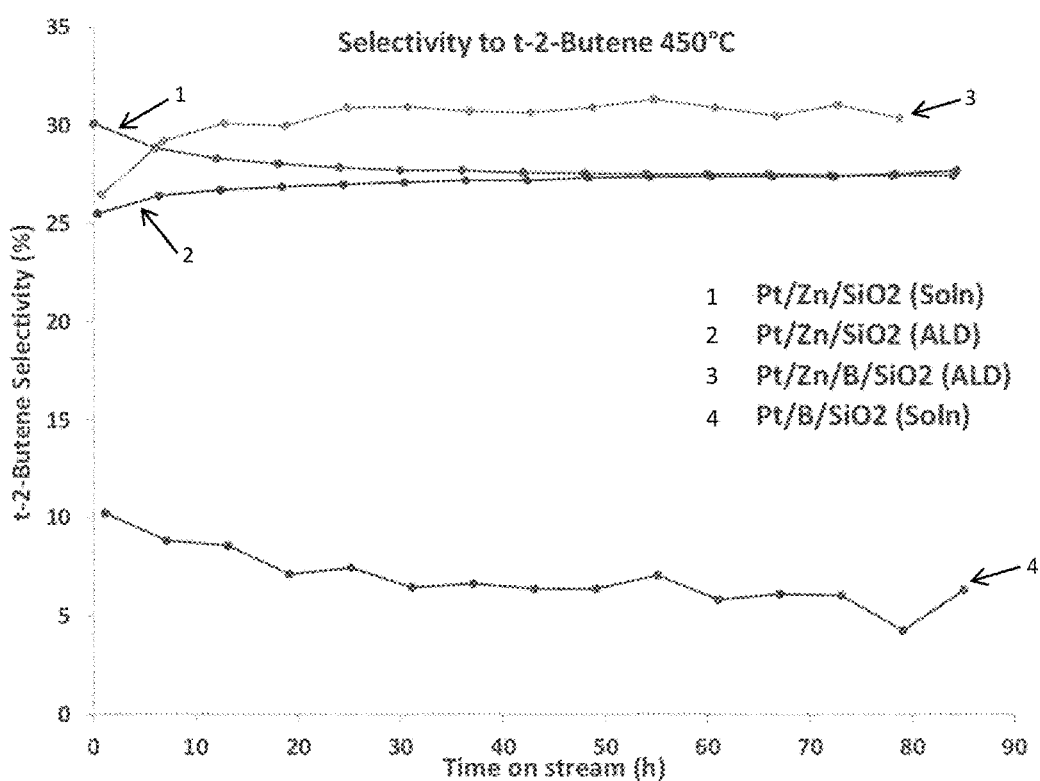
FIGS. 9A-9D show experimental results for different temperatures for selectivity to trans-2-butene from n-butane.
Figure 9B:
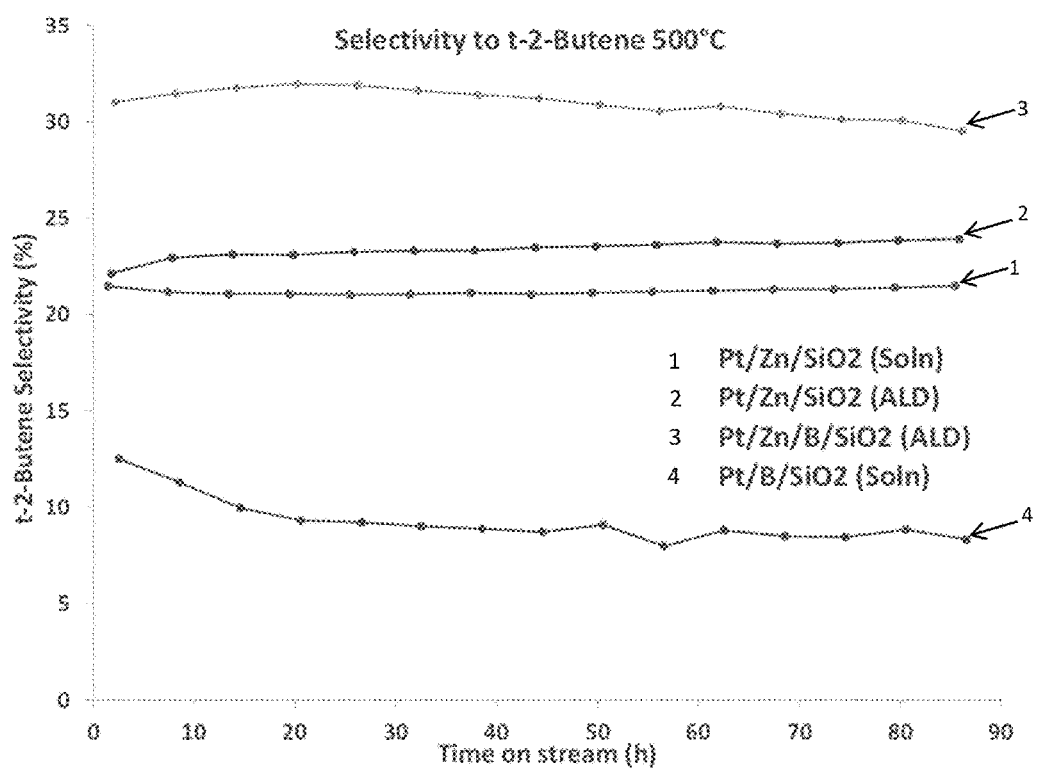
Figure 9C:
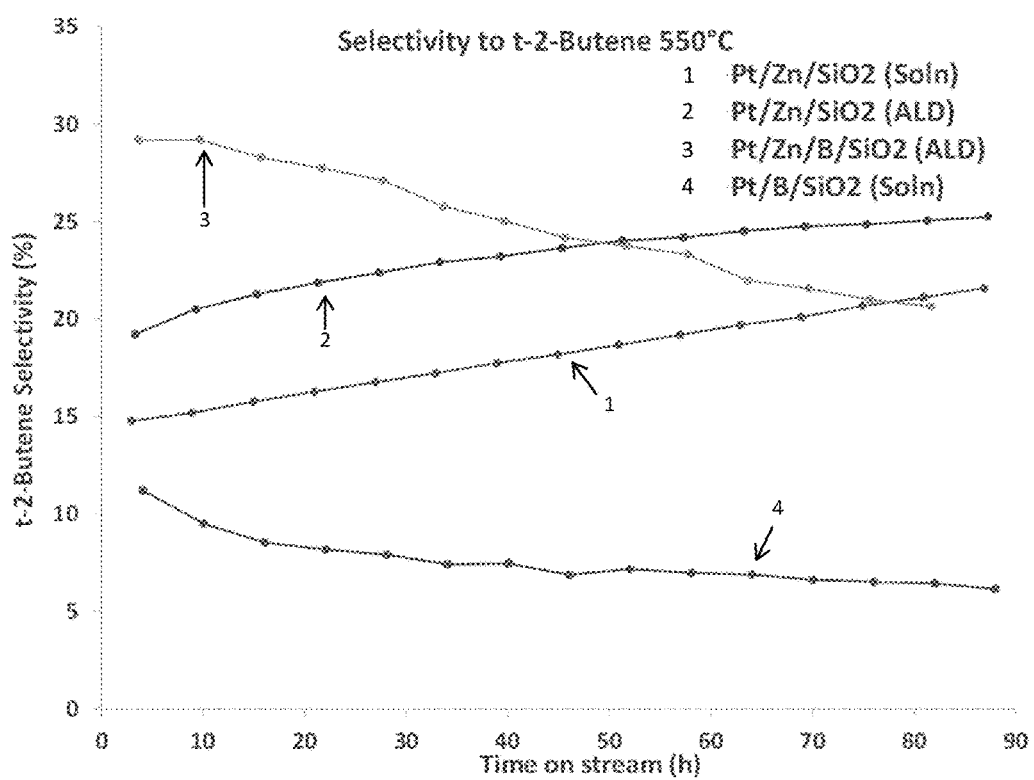
Figure 9D:
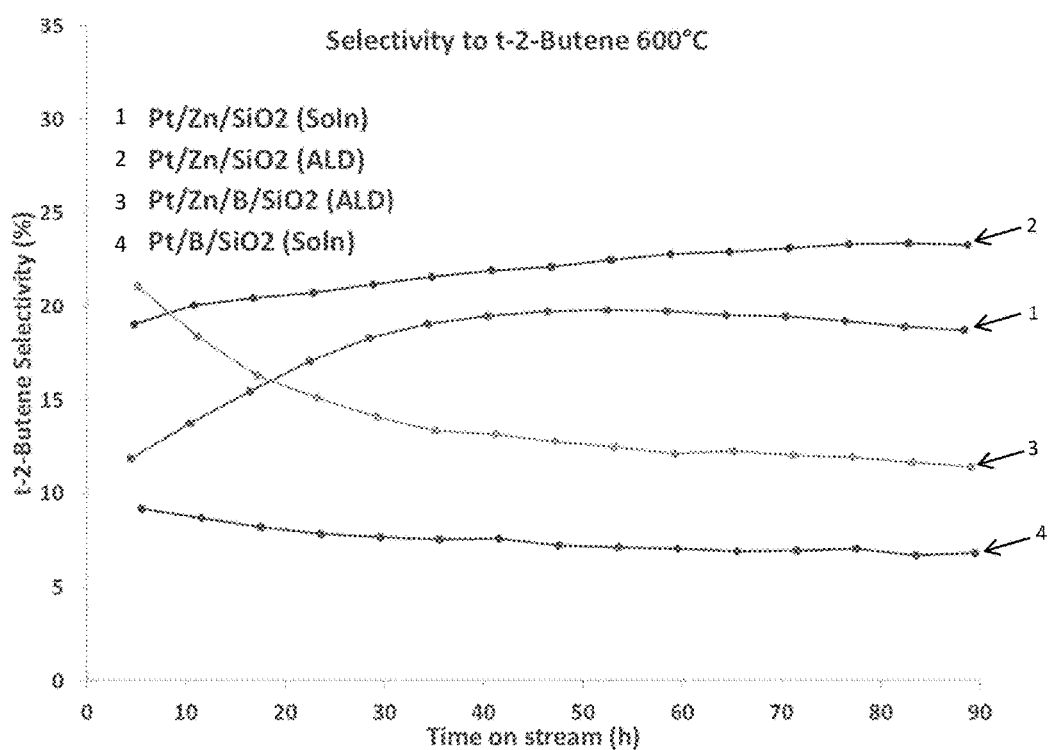
Figure 10A:
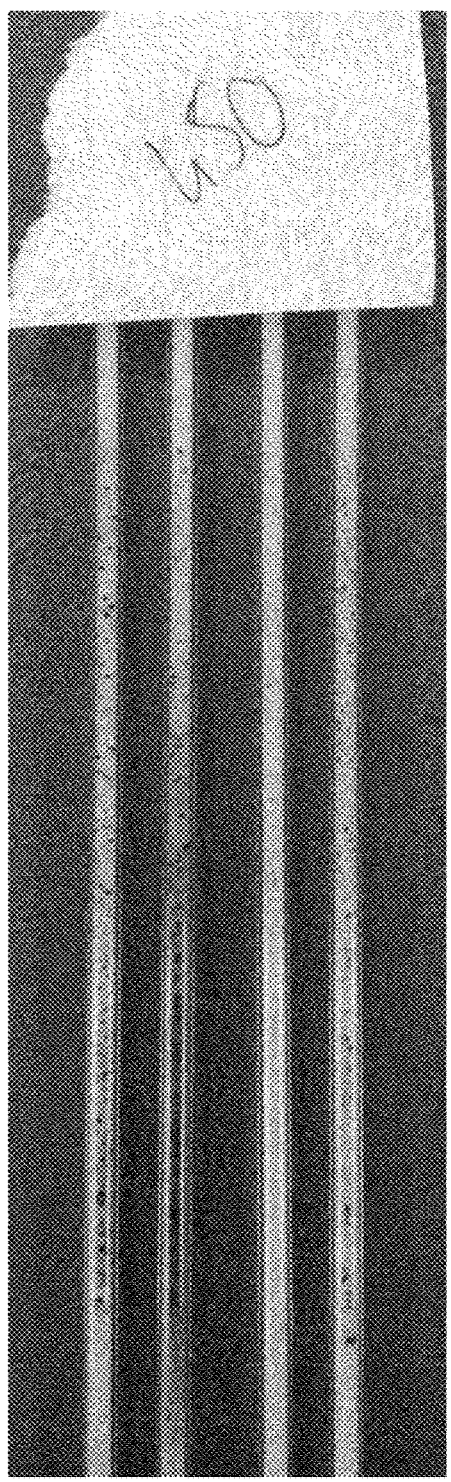
FIGS. 10A-10D show experimental results and the different degrees of coke deposition during n-butane dehydrogenation from left to right: Pt/Zn/SiO$_2$ (solution synthesis), Pt/Zn/SiO$_2$ (ALD synthesis), Pt/Zn/B/SiO$_2$ (ALD synthesis), Pt/B/SiO$_2$ (solution synthesis.
Figure 10B:
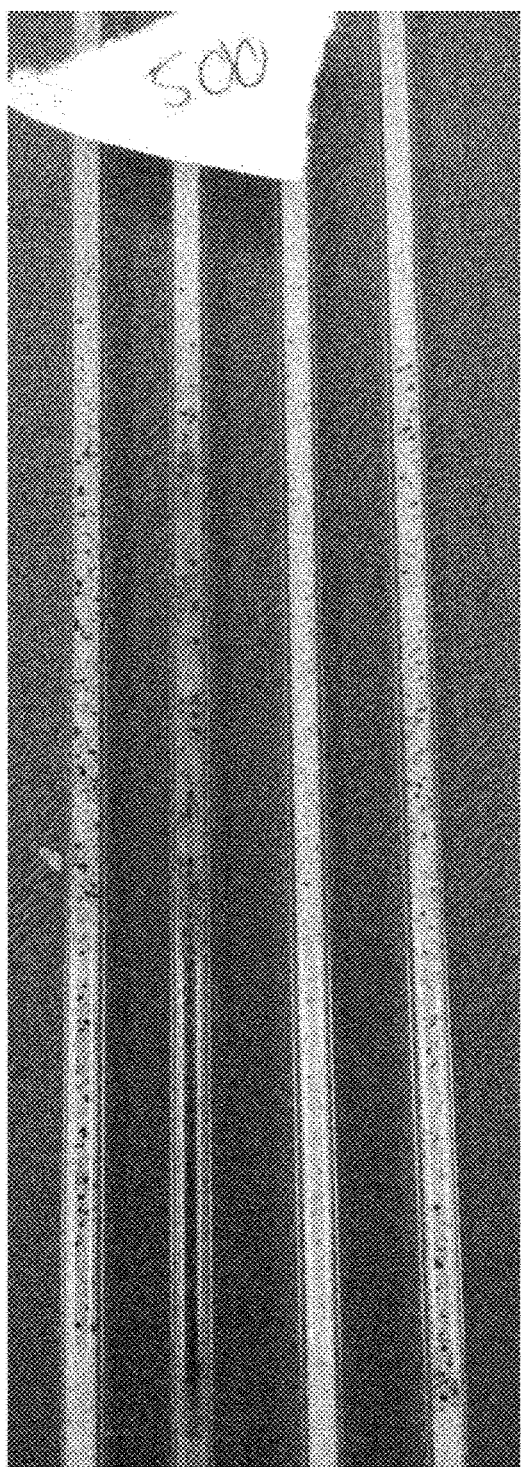
Figure 10C:
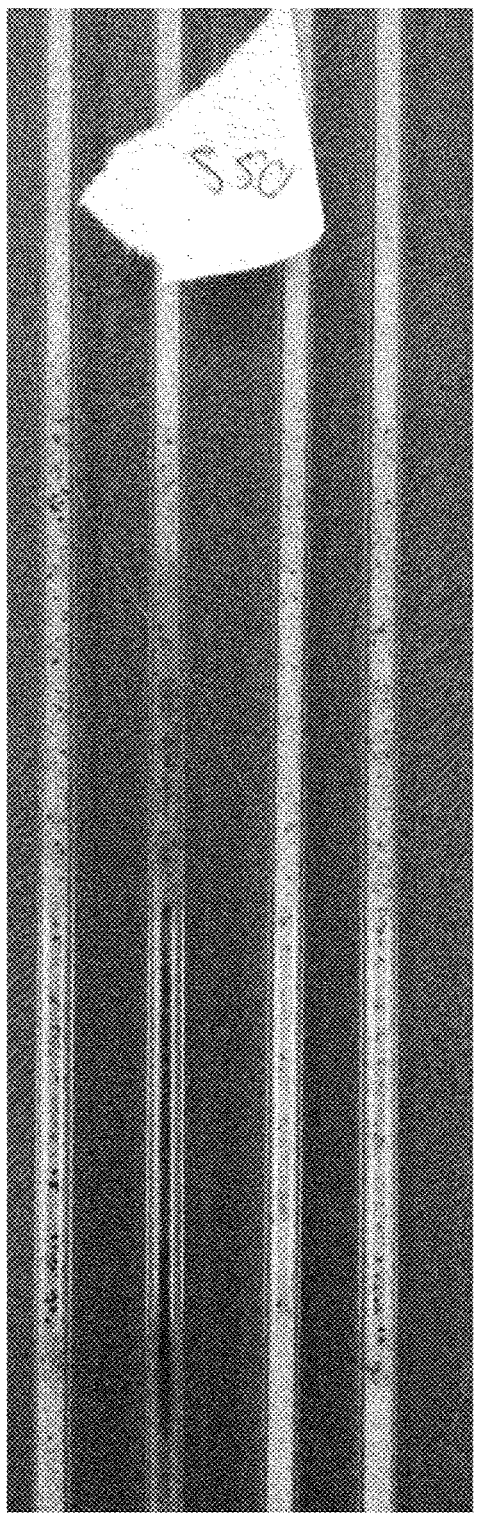
Figure 10D:
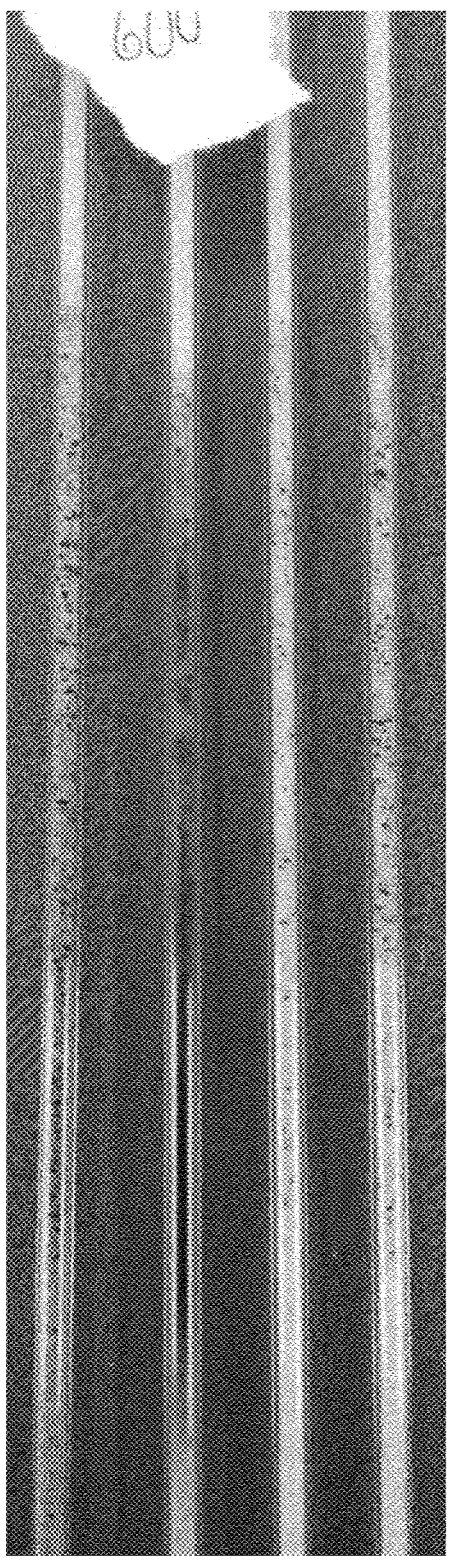

A first series of tests were performed with the following conditions:
 1% 1-butene in argon as feed stock.
 Temperatures (as indicated) of 500° C. or 600° C.
 Time length of about 70 hours
 Flow rates of 6.25 mL/min for the butene feedstock and 1.0 mL/min helium per reactor.
 10 mg of the indicated catalyst with 100 mg of SiO2 Davisil FIG. 3 shows the 1-butene conversion observed for the batch of catalysts tested; FIGS. 4A-4C show the selectivity of each catalyst to the four C4 products (1,3-butadiene, 1-butene, cis-2-butene and trans-2-butene).

Selectivity Profiles

FIGS. 4A-4C show the selectivity of each catalyst to the four C4 products (1,3-butadiene, 1-butene, cis-2-butene and trans-2-butene) at the optimum temperature (500° C.)

1-Butene Dehydrogenation Conclusions

A relatively lower selectivity to 1,3-butadiene was observed. It is believed this is due to competition with 1-butane isomerization to internal olefins. Catalysts remained active over an 80 hour test period. Dopants, such as boron, can be used to selective adjust selectivity, such as for internal butenes.

Coke Suppression

As stated above, coking of catalysts is a significant problem. Experiments where done to test coking suppression exhibited by certain catalysts. With respect to n-butane dehydrogenation, FIGS. 10A-10D illustrate visually the amount of coking for: Pt/Zn/SiO$_2$ fabricated by SEA (1); Pt/Zn/SiO$_2$ fabricated by ALD (2); Pt/Zn/B$_2$O$_3$/SiO$_2$ (i.e., boron doped) fabricated by ALD (3); and Pt/B$_2$O$_3$/SiO$_2$ fabricated by Soln (4). Generally, the boron-doped catalysts exhibited superior coke suppression to like-wise composed catalysts without the dopant. Further, the boron-doped catalysts exhibited enhanced thermal stability at the 600° C. temperature. ALD synthesis PT/Zn/B/SiO$_2$ performed the best in resisting coking.

Figure 11A:
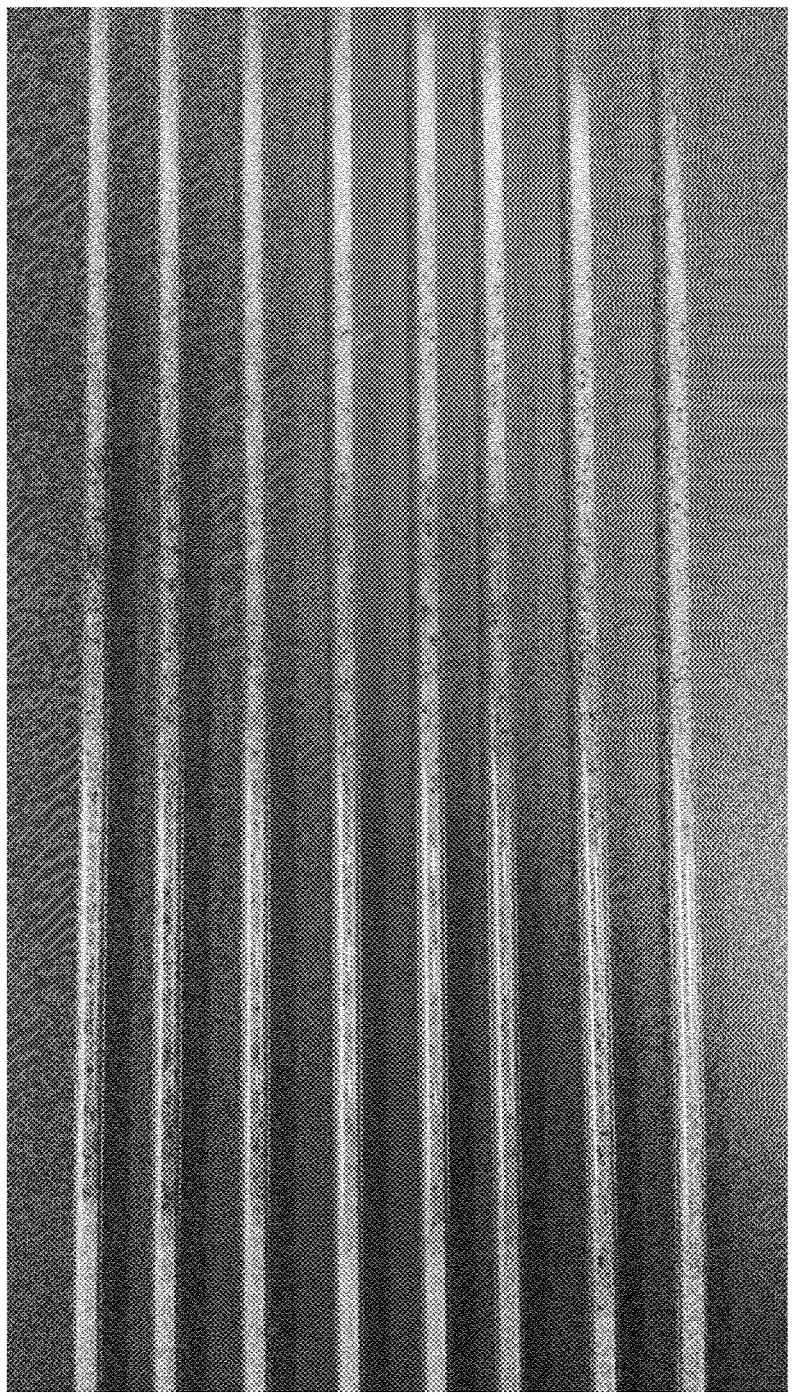
FIGS. 11A-11B show experimental results and the different degrees of coke deposition during n-butane dehydrogenation, from left to right: Pt/Zn/SiO2 (solution synthesis), Pt/Zn/SiO2 (ALD synthesis), Pt/Zn/B/SiO$_2$ (ALD synthesis), Pt(ALD)/B/SiO2 (ALD synthesis), Pt/B/SiO$_2$ (solution synthesis), Pt/B/SiO$_2$ (ALD synthesis), Zn/Pt/B/SiO$_2$ (ALD synthesis), Pt/Zn/Al$_2$O$_3$ (ALD synthesis).
Figure 11B:
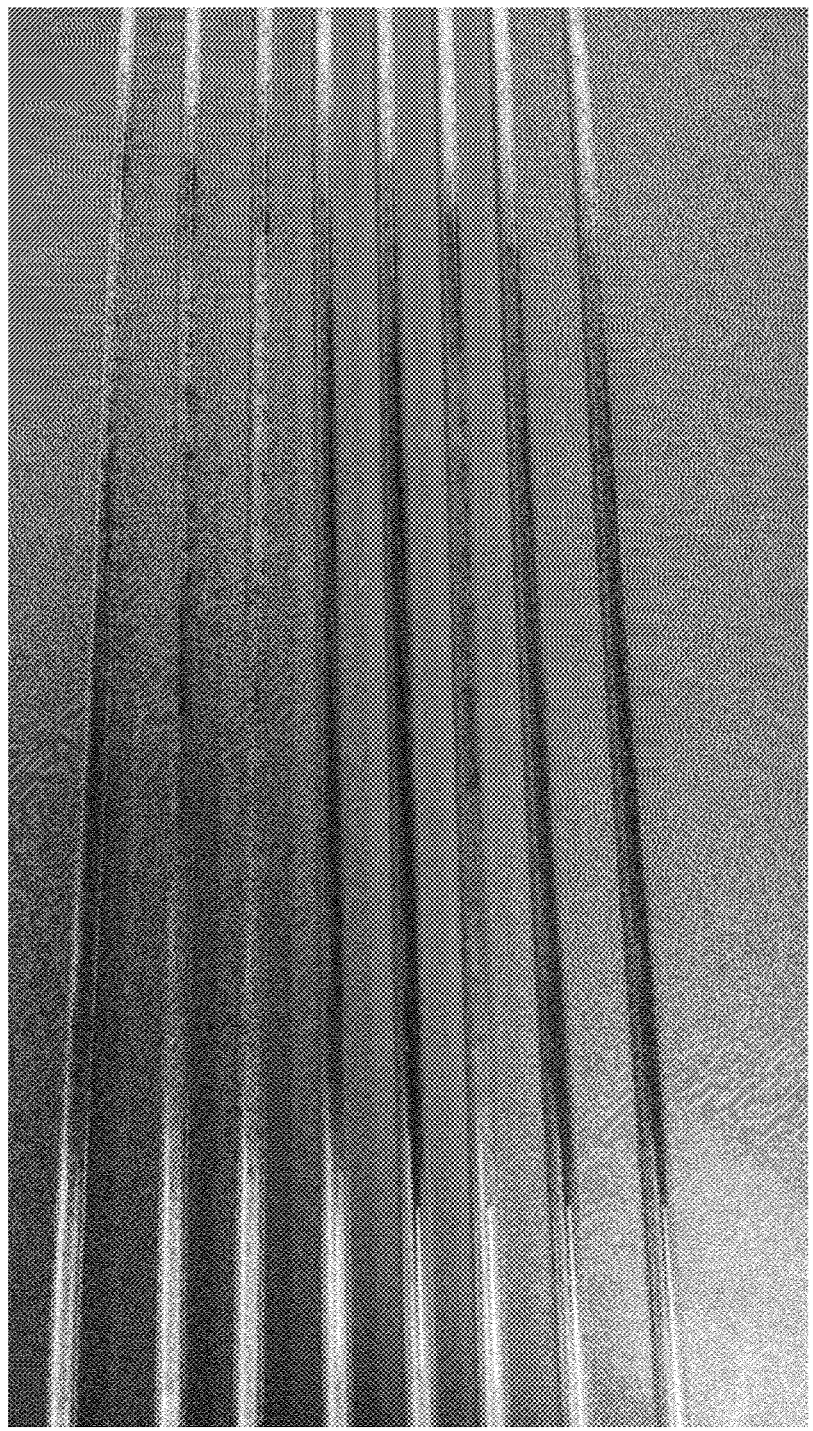

With respect to 1-butene dehydrogenation, FIGS. 11A-11B illustrate visually the amount of coking for: Pt/Zn/SiO$_2$ fabricated by Sol'n (1); Pt/Zn/SiO$_2$ fabricated by ALD (2); Pt/Zn/B/SiO$_2$ (i.e., boron-doped) fabricated by ALD (3); Pt (ALD)/B/SiO$_2$ (4); Pt/B/SiO$_2$ fabricated by Soln (5), Pt/Zn/B/SiO$_2$ (6); and ZnO/Pt/B/SiO$_2$ fabricated by Soln (7); and Pt/ZnO/Al$_2$O$_3$ (8).

With regard to coke suppression, PtZn exhibits good results for 1,3-butadiene production; PtB are more selective for butenes; and PtZnB shows the presence of boron suppresses coke formation The foregoing description of illustrative embodiments has been presented for purposes of illustration and of description. It is not intended to be exhaustive or limiting with respect to the precise form disclosed, and modifications and variations are possible in light of the above teachings or may be acquired from practice of the disclosed embodiments. It is intended that the scope of the invention be defined by the claims appended hereto and their equivalents.

What is claimed is:

1. A catalyst for n-butane dehydrogenation comprising:
    a substrate surface consisting essentially of an oxide;
    a promoter comprising an oxide consisting of MO$_x$ where M is a transition metal or main group elemental and x is greater than 0, the promoter deposited on the substrate;
    a catalytic material comprising a platinum group metal, a first dopant and a second dopant;
    the first dopant selected from the group consisting of Group 13 cations, Group 1 cations, and Group 2 cations;
    wherein the platinum group metal is between the promoter and the first dopant.

2. The catalyst of claim 1, wherein the catalyst exhibits 10-60% selectivity for 1,3 butadiene.

3. The catalyst of claim 1, wherein the catalyst exhibits 40-99% conversion of 1,3-butadiene.

4. The catalyst of claim 1, wherein the first dopant is boron.

5. The catalyst of claim 1, wherein the substrate comprises an oxide of a material selected from the group consisting of Si, Al, Ti, and Zn.

6. A method of forming 1,3 butadiene comprising:
    exposing n-butane to a catalyst comprising M$_1$/M'/M$_2$/E$_x$O$_y$, where the catalyst M' is a Pt group metal, M$_1$ is a first transition metal or a main group element material, M$_2$ is a second transition metal or a main group element material and E is Si, Al, Ti, or Zr and x and y represent stoichiometric amounts;
    forming 1,3 butadiene.

7. The method of claim 6 wherein forming the 1,3 butadiene comprises a selectivity for 1,3 butadiene of 10-60%.

8. The method of claim 6, wherein exposing the n-butane is at a temperature of between 250° C. and 650° C.

9. The method of claim 8, where the temperature is 500° C. to 600° C.

10. The method of claim 6, wherein exposing the n-butane comprises exposing the n-butane to at least 3.6 mg of catalyst.

11. The method of claim 10, wherein exposing the n-butane comprises exposing the n-butane to at least 13 mg of catalyst.

12. The method of claim 6, wherein the catalyst further comprises a group 13 dopant.

13. A method of forming 1,3 butadiene comprising:
    exposing 1-butene to a catalyst comprising a Pt group metal, first dopant consisting of a first transition metal or a main group element material, a second dopant consisting of a second transition metal or a main group element material and a substrate comprising an oxide of Si, Al, Ti, or Zr, the first dopant and the second dopant positioned between the substrate and the Pt group metal;
    forming 1,3 butadiene.

14. The method of claim 13, wherein forming the 1,3 butadiene comprises a selectivity for 1,3 butadiene of 10-60%.

15. The method of claim 13, wherein exposing the n-butane is at a temperature of between 250° C. and 650° C.

16. The method of claim 13, wherein the catalyst further comprises a group 13 dopant.

17. The catalyst of claim 1, wherein the promoter comprises a partial mono-layer on the substrate.

18. The catalyst of claim 1, wherein the promoter consists of isolated sites on the substrate.

19. The catalyst of claim 18, wherein the isolated sites are selected from the group consisting of clusters, islands, particles, and flakes.

* * * * *